US007875446B2

(12) United States Patent
Kang et al.

(10) Patent No.: US 7,875,446 B2
(45) Date of Patent: Jan. 25, 2011

(54) PURIFICATION PROCESSES FOR ISOLATING PURIFIED VESICULAR STOMATITIS VIRUS FROM CELL CULTURE

(75) Inventors: Yun Kang, Livingston, NJ (US); Mark William Cutler, Bloomingdale, NJ (US); Amadou Affrey Ouattara, New Milford, NJ (US); Kristen Elissa Syvertsen, Tarrytown, NY (US)

(73) Assignee: Wyeth LLC, Madison, NJ (US)

( * ) Notice: Subject to any disclaimer, the term of this patent is extended or adjusted under 35 U.S.C. 154(b) by 0 days.

(21) Appl. No.: 11/788,071

(22) Filed: Apr. 19, 2007

(65) Prior Publication Data

US 2007/0249019 A1 Oct. 25, 2007

Related U.S. Application Data

(60) Provisional application No. 60/793,376, filed on Apr. 20, 2006.

(51) Int. Cl.

| | |
|---|---|
| ***C12N 7/02*** | (2006.01) |
| ***C12N 1/02*** | (2006.01) |
| ***C12N 7/01*** | (2006.01) |
| ***A61K 39/205*** | (2006.01) |
| ***A61K 39/38*** | (2006.01) |
| ***A61K 39/12*** | (2006.01) |
| ***A01N 63/00*** | (2006.01) |
| *A61K 39/23* | (2006.01) |

(52) U.S. Cl. ................. 435/239; 424/224.1; 424/184.1; 424/204.1; 424/93.6; 424/93.1; 435/261; 435/235.1

(58) Field of Classification Search ....................... None
See application file for complete search history.

(56) References Cited

U.S. PATENT DOCUMENTS

| | | | | |
|---|---|---|---|---|
| 6,008,036 | A | 12/1999 | Fanget et al. | |
| 6,033,886 | A | 3/2000 | Conzelmann et al. | |
| 6,168,943 | B1 | 1/2001 | Rose | |
| 6,261,823 | B1 * | 7/2001 | Tang et al. | 435/239 |
| 7,326,555 | B2 * | 2/2008 | Konz et al. | 435/239 |
| 2003/0091592 | A1 * | 5/2003 | Barber | 424/199.1 |
| 2003/0175688 | A1 | 9/2003 | Pennathur-das et al. | |

FOREIGN PATENT DOCUMENTS

| | | | | |
|---|---|---|---|---|
| WO | WO 97/06243 | | | 2/1997 |
| WO | WO 03/078592 | A2 | | 9/2003 |
| WO | WO 03/093463 | A1 | | 11/2003 |
| WO | WO 2004/101765 | | | 5/2004 |
| WO | WO 2005/070953 | | | 8/2005 |
| WO | WO 2005/080556 | | * | 9/2005 |
| WO | WO 2005/098009 | A2 | | 10/2005 |
| WO | WO 2006/011580 | | | 2/2006 |

OTHER PUBLICATIONS

Pall Corporation (Online Publication of Dec. 1, 2005), Dynamic High Capacity Mustang® Q Membrane Units for Scaleable Anion Exchange Chromatography Purification of Adenoviral Vectors.*

Sartorius Corporation, Membrane Filter Cartridges, Sartobran P 0.2 um, Online Publication, 2003.*

Whatman Corporation, Product Guide, 2004-2005.*

Frazatti-Gallina et al., Vero-cell rabies vaccine produced using serum-free medium, 2004, Vaccine, vol. 23, pp. 511-517.*

Gallione et al., "Nucleotide sequences of the mRNA's encoding the vesicular Stomatitis virus N and NS proteins", J. Virol., Aug. 1981, 39(2):529-535.

Roberts et al., "Attenuated vesicular Stomatitis virus as vaccine vectors", J. Virol., May 1999, 73(5):3723-3732.

Robinson et al., "The nucleic acid of the bryan strain of rous sarcoma virus: purification of the virus and isolation of the nucleic acid", Biochemistry, Jul. 1965, 54:137-144.

Rose et al., "Nucleotide sequences of the mRNA's encoding the vesicular Stomatitis virus G and M proteins determined from cDNA clones containing the complete coding regions", J. Virol., Aug. 1981, 39(2):519-528.

Rose et al., "An effective AIDS vaccine based on live attenuated vesicular Stomatitis virus recombinants", Cell, Sep. 7, 2001, 106:539-549.

Schlereth et al., "Successful vaccine-induced seroconversion by single-dose immunization in the presence of measles virus-specific maternal antibodies", J. Virol., May 2000, 74(10):4652-4657.

Zolotukhin et al., "Recombinant adeno-associated virus purification using novel methods improves infectous titer and yield", Gene Therapy, Jun. 1999, 6:973-985.

Burkhart, Christoph et al., "Characterization of T-Helper Epitopes of the Glycoprotein of Vesicular Stomatitis Virus", Journal of Virology, vol. 68, No. 3, 1994, pp. 1573-1580.

de las Mercedes Segura, Maria et al., "Downstream processing of oncoretroviral and lentiviral gene therapy vectors", Biotechnology Advances, vol. 24, 2006, pp. 321-337.

Morenweiser, R., "Downstream processing of viral vectors and vaccines", Gene Therapy, vol. 12, 2005, pp. S103-S110.

(Continued)

*Primary Examiner*—Zachariah Lucas
*Assistant Examiner*—Benjamin P Blumel

(57) ABSTRACT

A process is described for purifying vesicular stomatitis virus (VSV) from cell culture fluid of a mammalian cell culture infected with VSV, the process comprising: clarifying the cell culture fluid by low-speed centrifugation and recovering the VSV in the supernatant; filtering the supernatant through a 0.2 to 0.45 μm filter and recovering the VSV in the filtered solution; loading the VSV filtered solution onto a anion exchange membrane adsorber equilibrated with a first pH buffered salt solution, eluting the VSV from the anion exchange membrane adsorber with a second pH buffered salt solution and recovering the eluted VSV fractions; purifying the recovered VSV by tangential flow filtration (TFF) using a TFF membrane having a molecular weight cutoff between 300 kDa and 1,000 kDa and recovering the VSV in the retentate, and filtering the VSV retentate through a 0.2 to 0.22 μm filter and recovering the VSV in the filtered solution.

20 Claims, 8 Drawing Sheets

OTHER PUBLICATIONS

Scherr, M. et al., "Efficient gene transfer into the CNS by lentiviral vectors purified by anion exchange chromatography", Gene Therapy, vol. 9, 2002, pp. 1708-1714.

Hecht, T. et al., "Limitation of VSV infection by the host's response to VSV-associated cellular antigens", The Journal of Immunology, vol. 129, No. 4, 1982, pp. 1736-1741.

Brown et al., "Structure and immunogenicity of antigens derived from the virion by treatment with Tween and ether", J. Immun., 99(1):171-177, 1967.

Downing et al., "Active respiratory syncytial virus purified by ion-exchange chromatography: characterization of binding and elution requirements", Journal of Virological Methods, 38(2):215-228, Aug. 1992.

Endres et al., "Evaluation of an ion-exchange membrane for the purification of plasmid DNA", Biotechnology and Applied Biochemistry, 37(3):259-266, Jun. 2003.

Rabotti & Teutsch et al., "The Immunologic determinants in the system of avian oncogenic virus. Purification and immunochemical characterization of the antigen for the group in chick cells transformed by Rous sarcoma virus (Schmidt-Ruppin strain)", Comptes Rendus des Seances de l'Academie des Sciences, Serie D: Sciences Naturelles, 272(2):343-346, Jan. 11, 1971.

Haber et al., "Membrane chromatography of DNA: Conformation-induced capacity and selectivity", Biotechnology and Bioengineering, 88(1):26-34, Oct. 5, 2004.

Jacoli, "Purification of turnip mosaic virus by gel filtration", Biochimica et Biophysica Acta, General Subjects, 165(2):299-302, Sep. 3, 1968.

KÅrsnäs et al., "Bovine viral diarrhea virus: purification of surface proteins in detergent-containing buffers by fast protein liquid chromatography", Journal of Chromatography, 266:643-649, Aug. 26, 1983.

Kanani et al., "Protein bioseparation by membrane chromatography using polyelectrolyte gel-coated adsorptive membranes", AIChE Annual Meeting, Conference Proceedings, Austin, TX, United States, Nov. 7-12, 2004.

Kristiansen et al., "Virus purification by Vicia ervilia lectin coupled to Sepharose", Protides of the Biological Fluids, 23:663-665, 1976.

Lu et al., "Purification of Hemoglobin by Ion Exchange Chromatography in Flow-Through Mode with PEG as an Escort", Artificial Cells, Blood Substitutes, and Biotechnology, 32(2):209-227, May 2004.

McSharry & Benzinger, "Concentration and purification of vesicular stomatitis virus by polyethylene glycol precipitation", Virology, 40(3):745-746, Mar. 1970.

Menard et al., "Bovine leukemia virus: purification and characterization of the aspartic protease", Virology, 193(2):680-689, Apr. 1993.

Nishimura & Kitaoka, "Purification of Japanese encephalitis virus and its antigenic particles from infected suckling mouse brains", Japanese Journal of Medical Science & Biology, 17:295-305, Dec. 1964.

Nochumson et al., "Use of ion-exchange membrane adsorbers for production of biopharmaceuticals", Abstracts of Papers, 221st ACS National Meeting, San Diego, CA, United States, COLL-442, Apr. 1-5, 2001.

Pora & Hall, "Use of ion-exchange membrane adsorbers for production of biopharmaceuticals", Animal Cell Technology: From Target to Market, Proceedings of the ESACT Meeting, 17th, Tyloesand, Sweden, 466-468, Jun. 10-14, 2001.

Roberts et al., "Vaccination with a Recombinant Vesicular Stomatitis Virus Expressing an Influenza Virus Hemagglutinin Provides Complete Protection from Influenza Virus Challenge", Journal of Virology, 72(6):4704-4711, Jun. 1998.

Specht et al., "Densonucleosis virus purification by ion exchange membranes", Biotechnology and Bioengineering, 88(4):465-473, Nov. 20, 2004.

Teeters et al., "Adsorptive membrane chromatography for purification of plasmid DNA", Journal of Chromatography, A, 989(1):165-173, Mar. 7, 2003.

Transfiguracion et al., "Size-Exclusion Chromatography Purification of High-Titer Vesicular Stomatitis Virus G Glycoprotein-Pseudotyped Retrovectors for Cell and Gene Therapy Applications", Human Gene Therapy, 14(12):1139-1153, Aug. 10, 2003.

Vellekamp et al., "Empty capsids in column-purified recombinant adenovirus preparations", Human Gene Therapy, 12(15):1923-1936, Oct. 10, 2001.

Yamada et al., "Lentivirus vector purification using anion exchange HPLC leads to improved gene transfer", BioTechniques, 34(5):1074-1078 and 1080, May 2003.

Yang et al., "Purification of a large protein using ion-exchange membranes", Industrial & Engineering Chemistry Research, 41(6):1597-1602, 2002.

Zeng, "Effective applications of membrane chromatographic processes in biotechnology: Case studies", Abstracts of Papers, 227th ACS National Meeting, Anaheim, CA, United States, BIOT-368, Mar. 28-Apr. 1, 2004.

Zhang et al., "Large-scale capture and partial purification of plasmid DNA using anion-exchange membrane capsules", Biotechnology and Applied Biochemistry, 37(3):245-249, Jun. 2003.

* cited by examiner

```
Cell Culture Fluid
        │
        ▼
┌─────────────────────┐
│  1° Clarification   │
│ Speed Centrifugation│
└─────────────────────┘
        │
        ▼
┌─────────────────────┐
│  2° Clarification   │
│     Filtration      │
└─────────────────────┘
        │
        ▼
┌─────────────────────┐
│   Anion Exchange    │
│  Membrane Adsorber  │
└─────────────────────┘
        │
        ▼
┌─────────────────────┐
│Tangential Flow Filtration│
└─────────────────────┘
        │
        ▼
┌─────────────────────┐
│     Filtration      │
└─────────────────────┘
        │
        ▼
    Purified VSV
   Bulk Concentrate
```

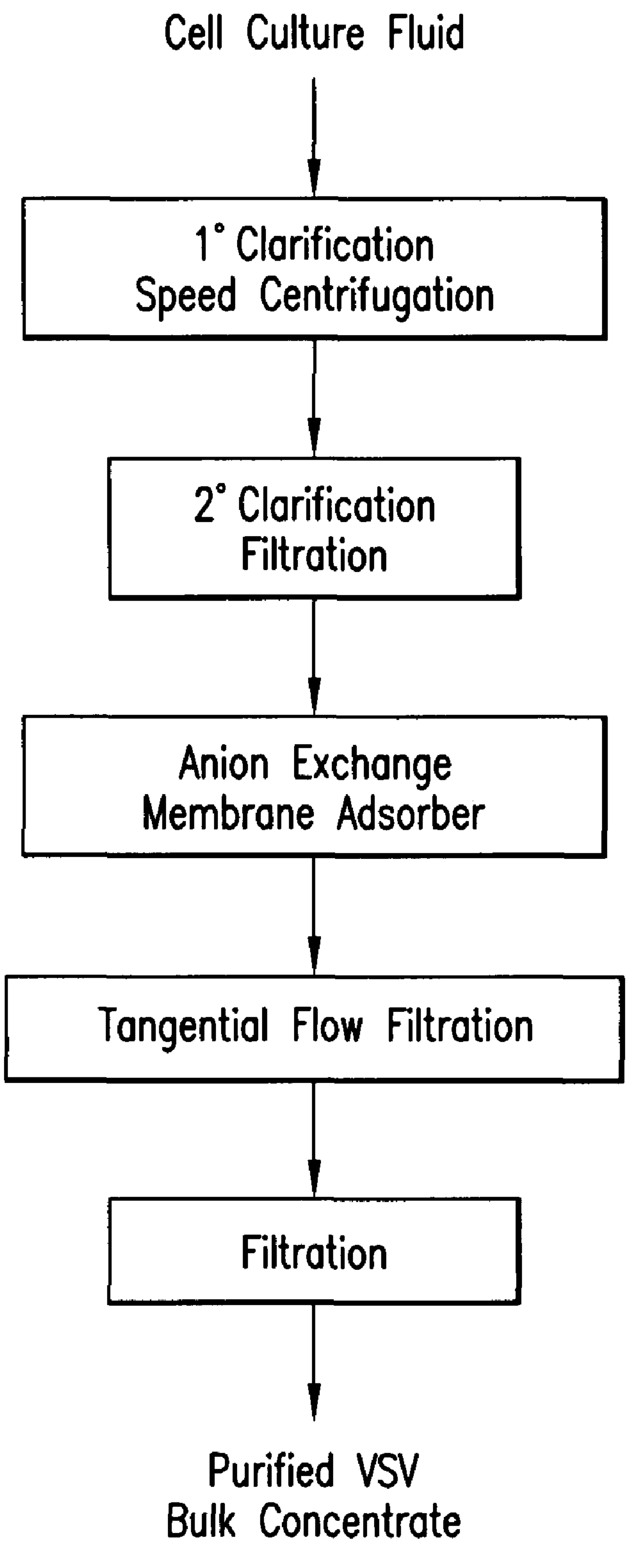

FIG. 1

PURIFICATION PROCESSES FOR ISOLATING PURIFIED VESICULAR STOMATITIS VIRUS FROM CELL CULTURE

CROSS-REFERENCE TO RELATED APPLICATION

This application claims the benefit of the priority of U.S. provisional patent application No. 60/793,376, filed Apr. 20, 2006.

BACKGROUND OF THE INVENTION

Vesicular stomatitis virus (VSV), a member of the Rhabdoviridae family, has a non-segmented, negative-sense, single-stranded RNA genome. Its eleven kb genome has five genes which encode five structural proteins of the virus: the nucleocapsid protein (N), which is required in stoichiometric amounts for encapsidation of the replicated RNA; the phosphoprotein (P), which is a cofactor of the RNA-dependent RNA polymerase (L); the matrix protein (M) and the attachment glycoprotein (G) (e.g., see Gallione et al., 1981 J. Virol., 39:529-535; Rose and Gallione, 1981, J. Virol., 39:519-528; U.S. Pat. No. 6,033,886; U.S. Pat. No. 6,168,943).

In general, VSV is not considered a human pathogen, and as such, pre-existing immunity to VSV is rare in the human population. Thus, the development of VSV derived vectors has been a focus in areas such as immunogenic compositions. (e.g., vaccines) and the delivery of genes encoding therapeutic proteins. For example, studies have established that VSV can serve as an effective vector for expressing influenza virus haemagglutinin protein (Roberts et al., 1999 J. Virol., 73:3723-3732), measles virus H protein (Schlereth et al., 2000 J. Virol., 74:4652-4657) and HIV-1 env and gag proteins (Rose et al., 2001 Cell, 106(5):539-49). Other characteristics of VSV that render it an attractive vector include: (a) the ability to replicate robustly in cell culture; (b) the inability to either integrate into host cell DNA or undergo genetic recombination; (c) the existence of multiple serotypes, allowing the possibility for prime-boost immunization strategies; (d) foreign genes of interest can be inserted into the VSV genome and expressed abundantly by the viral transcriptase; and (e) the development of a specialized system for the rescue of infectious virus from a cDNA copy of the virus genome (e.g., see U.S. Pat. No. 6,033,886; U.S. Pat. No. 6,168,943).

The production of VSV vectored immunogenic compositions generally includes infecting a suitable cell culture (host) with recombinant VSV, growing VSV in cell culture, harvesting the cell culture fluid at the appropriate time and purifying the VSV from the cell culture fluid. The use of VSV vectors, and immunogenic compositions thereof, in clinical applications will require VSV samples (or doses) of appropriate purity in order to comply with safety regulations of the various drug safety authorities around the world (e.g., the Food and Drug Administration (FDA), the European Medicines Agency (EMEA), the Canadian Health Products and Food Branch (HPFB), etc.).

However, it is typically difficult to separate VSV from the cell culture contaminants (e.g., cell culture impurity proteins and DNA) and obtain VSV of appropriate purity and yield using the currently available VSV purification processes (e.g., purification via sucrose gradient centrifugation). For example, using the currently available purification processes, there is typically an inverse relationship between the purity and recovery (percent yield) of VSV samples, thereby making it difficult to manufacture sufficient quantities of purified VSV. Additionally, in today's bioreactor-based processes, increased cell concentrations and longer culture times result in higher VSV titers, with concomitant increases in cell debris and concentrations of organic constituents in the bioreactor fluid, further complicating VSV purification processes.

Sucrose gradient ultracentrifugation has been the standard method for virus purification (including VSV purification) since 1964 (Yamada et al., 2003 BioTechniques, 34(5):1074-1078, 1080; Brown et al., 1967 J. Immun., 99(1):171-7; Robinson et al., 1965 Proc. Natl. Acad. Sci., USA, 54(1):137-44; Nishimura et al., 1964 Japan. J. Med. Sci. Biol., 17(6):295-305). However, as virus concentrations increase, concomitant increases in cell debris, host DNA and protein impurities also occur, which are very difficult to remove at higher concentrations via sucrose gradient ultracentrifugation. In addition, sucrose gradient ultracentrifugation is extremely costly to scale-up. Concentration and purification of VSV by polyethylene glycol (PEG) precipitation (McSharry et al., 1970 Virol., 40(3):745-6) has similar problems of high impurity levels.

Relatively high quality virus has been obtained via size exclusion chromatography (Transfiguracion et al., 2003 Human Gene Ther., 14(12):1139-1153; Vellekamp, et al., 2001 Human Gene Ther., 12(15):1923-36; Rabotti et al., 1971 Comptes Rendus des Seances de l'Academie des Sciences, Serie D: Sciences Naturelles, 272(2):343-6; Jacoli et al., 1968 Biochim. Biophys. Acta, Genl Subj., 165(2):99-302). However, due to process cost and operating difficulty, it is generally not feasible for large-scale virus production. Affinity chromatography, such as heparin (Zolotukhin et al., 1999 Gene Ther., 6(6):973-985), lectin (Kaarsnaes et al., 1983 J. Chromatog., 266:643-9; Kristiansen et al., 1976 Prot. Biol. Fluids, 23:663-5) and Matrex™ Cellufine™ sulfate (Downing et al., 1992 J. Virol. Meth., 38(2):215-228), has found some application in virus purification. Heparin and lectin are generally not preferred (or used) for cGMP virus production due to possible leaching problems, which would require additional tests prior to product release.

Affinity purification of virus using Matrex™ Cellufine™ sulfate is an unresolved issue, due to efficiency of virus purification, virus quality and column regeneration. For VSV purification, very large affinity columns are needed (e.g., 0.2 L Matrex™ Cellufine™ sulfate resin per liter of cell culture; Wyeth Vaccine unpublished results). Low virus yield was observed when purified via ion exchange chromatography, either alone, or in combination with other types of traditional chromatographic techniques used in virus purification (International Patent Publication No. WO2006/011580; Specht et al., 2004 Biotech. Bioeng., 88(4):465-173; Yamada et al., 2003, cited above; Vellekamp et al., 2001 cited above; Zolotukhin et al., 1999, cited above; (International Patent Publication No. WO1997/06243; Kaarsnaes et al., 1983, cited above).

Thus, there is a current and ongoing need in the art for purification processes which can generate VSV at an appropriate level of purity and recovery (yield).

SUMMARY OF THE INVENTION

The processes and compositions described herein generally relate to the fields of virology, microbiology, immunology and process development. More particularly, novel purification processes for obtaining vesicular stomatitis virus (VSV) of improved purity and yield are described.

In one aspect, a process for purifying VSV from cell culture fluid of a mammalian cell culture infected with VSV comprises the steps of: (a) primary clarification, (b) secondary clarification, (c) anion exchange membrane adsorbtion, (d)

tangential flow filtration and (e) filtration. In one embodiment, step (a) comprises clarifying cell culture fluid by low-speed centrifugation and recovering the VSV in the supernatant. In one embodiment, step (b) comprises filtering the supernatant through a 0.2 to 0.45 μm filter and recovering the VSV in the filtered solution. In another embodiment, step (c) comprises loading the VSV filtered solution onto an anion exchange membrane adsorber equilibrated with a first pH buffered salt solution, eluting the VSV from the anion exchange membrane adsorber with a second pH buffered salt solution, and recovering the eluted VSV fractions. In one embodiment, step (d) comprises purifying the recovered VSV by tangential flow filtration (TFF) using a hollow fiber membrane having a molecular weight cutoff between 300 kDa and 1,000 kDa, and recovering the VSV in the retentate. In one embodiment, step (e) comprises filtering the VSV retentate through a 0.2 to 0.22 μm filter and recovering the VSV in the filtered solution.

In certain embodiments, the cells of the mammalian cell culture are selected from human embryonic kidney (HEK) cells, HEK 293 cells, Chinese hamster ovary (CHO) cells, baby hamster kidney (BHK) cells and African green monkey kidney (AGMK) cells, also known as Vero cells.

In certain embodiments, the low-speed centrifugation step of the purification process is between 4,400×g to 8,000×g. In one particular embodiment, the low-speed centrifugation is 6,238×g.

In another embodiment, the 0.2 to 0.45 μm filter is a Millipore Millex®-GV filter unit, a Millipore Millex®-GP filter unit, a Pall Supor® filter unit, a Sartorius Sartobran™ filter unit or a Sartorius Sartopore™ 2 filter unit. In one particular embodiment, the filter is a 0.2 μm Sartorius Sartobran™ filter unit.

In other embodiments, the anion exchange membrane adsorber is a Sartorius Sartobind™ Q membrane adsorber or a Pall Mustang™ Q membrane adsorber. In one particular embodiment, the anion exchange membrane adsorber is a Pall Mustang™ Q membrane adsorber.

In certain other embodiments, the salt in the first pH buffered salt solution in step (c) is NaCl or KCl. In another embodiment, the ionic strength of the NaCl or KCl is 0.1 M to 0.4 M. In one particular embodiment, the salt is NaCl and the ionic strength of the NaCl is 0.3 M.

In another embodiment, the salt in the second pH buffered salt solution in step (c) is NaCl or KCl. In one particular embodiment, the salt in the second pH buffered salt solution is NaCl. In one particular embodiment, the ionic strength of the NaCl in the second pH buffered salt solution is between 0.5 M to 0.75 M. In another particular embodiment, the ionic strength of the NaCl in the second pH buffered salt solution is 0.6 M. In yet other embodiments, the ionic strength of the NaCl in the second pH buffered salt solution is 0.75 M. In certain other embodiments, the second pH buffered salt solution has an elution flow rate of 10 capsule volumes/minute (CV/minute) to 30 CV/minute. In yet other embodiments, the elution flow rate is 20 CV/minute.

In certain other embodiments, the ionic strength of the NaCl in the second pH buffered salt solution is linearly increased from 0.001 M to 0.75 M at an elution flow rate of 10 CV/minute to 30 CV/minute. In one particular embodiment, the linear elution gradient flow rate is 20 CV/minute.

In yet other embodiments, the first and second buffers of step (c) have a pKa between 6.0 to 8.5. In still other embodiments, the first pH buffered salt solution of step (c) has a pH of 6.5 to 8.0. In one particular embodiment, the first pH buffered salt solution has a pH of 7.5. In other embodiments, the second pH buffered salt solution of step (c) has a pH of 6.5 to 8.0. In one particular embodiment, the second pH buffered salt solution has a pH of 7.5.

In certain other embodiments, the first and second buffers of step (c) are phosphate buffer, N-2-Hydroxyethylpiperazine-N'-2-ethanesulfonic acid (HEPES) buffer or Tris(hydroxymethyl)aminomethane (TRIS). In another embodiment, the first and second pH buffered salt solutions of step (c) further comprise sucrose at a concentration of 1.5% to 5%. In one particular embodiment, the sucrose concentration is 2%.

In certain other embodiments, the TFF membrane has a 300 kDa molecular weight cutoff. In yet other embodiments, the TFF membrane has a 750 kDa molecular weight cutoff. In yet other embodiments, the TFF membrane has at least a 350, 400, 450, 500, 550, 600, 650, 700, 800, 850, 900, 950 or 1,000 kDa molecular weight cutoff. In one particular embodiment, the TFF membrane is a hollow fiber membrane module. In another embodiment, the TFF comprises concentrating the VSV recovered from step (c) at least 5×, followed by at least one buffer exchange. In still another embodiment, the TFF comprises concentrating the VSV recovered from step (c) at least 5×, followed by at least five buffer exchanges. In one particular embodiment, the buffer used in the buffer exchange is a phosphate buffer, HEPES buffer or TRIS buffer, wherein the buffer has a concentration of 5 mM to 15 mM and a pH of 7.2 to 7.5. In another embodiment, the buffer exchange buffer further comprises 0.10 M to 0.20 M NaCl and 3.5% to 4.5% sucrose.

In other embodiments, the purification process steps (a) through (e) are performed at room temperature, wherein room temperature is defined as a temperature or temperatures on or between about 15° C. to about 25° C. In one particular embodiment, the purification process steps (a) through (e) are performed at 20° C.

In yet another embodiment, the clarifying of the cell culture fluid in step (a) is by a 1.0 μm to 4.5 μm depth filtration module, wherein low-speed centrifugation is omitted from step (a). In specific embodiments, the depth filtration module is a Whatman® Polycap™ HD module, a Sartorius Sartoclear™ P module or a Millipore® Millistak+® HC module.

In another aspect, VSV of improved purity are obtained from mammalian cell culture. In certain embodiments, the purified VSV is at least 90.0% free of cell culture protein and nucleic acid contaminants. In other embodiments, the purified VSV is 99.0% free of cell culture protein and nucleic acid contaminants. In one particular embodiment, the purified VSV is 99.8% free of cell culture protein and nucleic acid contaminants.

In certain other embodiments, VSV of improved purity is provided, which is purified and isolated according to the novel purification processes described herein. In certain embodiments, the purified VSV is characterized by one or more of the following characteristics: a selected VSV serotype or combination of serotypes; a genomic sequence comprising at least one mutation or at least two mutations, which attenuate the pathogenicity of VSV, a genomic sequence comprising a foreign polynucleotide sequence open reading frame (ORF) sequence encoding one or more of a variety of proteins (therapeutic or immunogenic) recited in detail in the detailed description portion of the specification.

Other features and advantages of the compositions and processes described herein will be apparent from the following detailed description, from the preferred embodiments thereof, and from the claims.

BRIEF DESCRIPTION OF THE FIGURES

FIG. 1 is a flow chart showing the purification process (outlined in black boxes) for obtaining VSV of improved purity from mammalian cell culture fluid.

DETAILED DESCRIPTION OF THE INVENTION

Figure 2B:
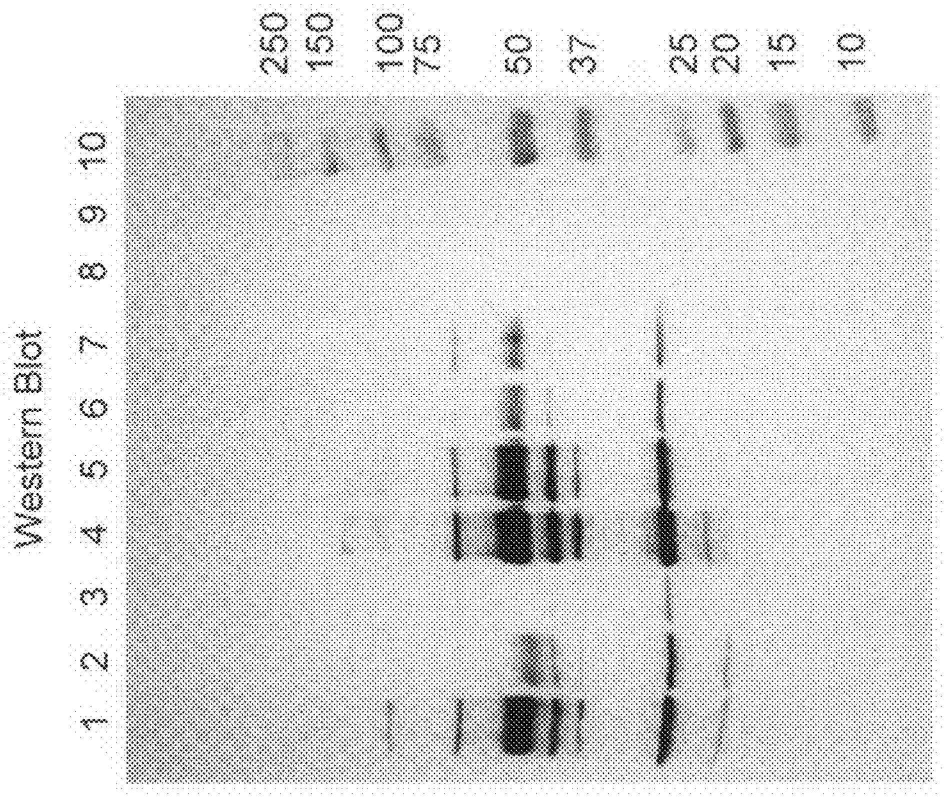
FIG. 2B is an electrophoretic gel showing the separation of VSV proteins by Western blot, according to the description of FIG. 2A. The Western Blot detection was with anti-VSV polyclonal antibodies.

Because vesicular stomatitis virus (VSV) has many characteristics which make it an appealing vector for use in immunogenic compositions and/or the delivery of genes encoding therapeutic proteins as described above, there is an ongoing need in the art for purification processes that generate recombinant VSV of improved purity from mammalian cell culture. The compositions and processes described hereinafter address that need. As set forth below in Examples 3-8, improved processes for purifying VSV from mammalian cell culture (e.g., see FIG. 1) and VSV purified thereby are described.

I. Production of VSV in a Mammalian Cell Culture

The production of VSV in mammalian cell culture is well known to one of skill in the art, and generally includes infecting the cell culture (host cell) with recombinant VSV, growing the VSV in cell culture and harvesting the cell culture at the appropriate time. Because VSV is secreted from the host cell into the media, the VSV product is collected from the cell culture fluid.

The production of VSV from mammalian cell culture, and thus the novel processes for purifying VSV therefrom as described herein, employ suitable mammalian cell cultures used to propagate (or grow) VSV (a non-segmented, negative-sense, single-stranded RNA virus), which are known in the art. Such cell cultures include, but are not limited to, human embryonic kidney (HEK) cells such as HEK 293 cells, African green monkey kidney (AGMK) cells such as Vero cells, Chinese hamster ovary (CHO) cells and baby hamster kidney (BHK) cells.

Additionally, cell culture materials, methods and techniques are well known to one of skill in the art. For example, a recombinant VSV seed stock (e.g., a rescued VSV, see Section II below) is used to infect a confluent host cell population or a host cell population at a certain density (e.g., a Vero cell culture) in a bioreactor at a given multiplicity of infection, the VSV is grown in cell culture for a given time and temperature; and the nascent VSV progeny harvested in the cell culture fluid. As defined hereinafter, the terms "culture fluid", "cell culture fluid", "cell culture media", "media" and/or "bioreactor fluid" are used interchangeably, and refer to the media or solution in which the cell culture is grown.

II. Purification of VSV from a Mammalian Cell Culture

The novel processes for purifying VSV from cell culture fluid of a mammalian cell culture infected with VSV described herein comprise certain purification steps. The flow chart in FIG. 1 outlines the overall purification scheme, which includes the steps of (a) primary clarification, (b) secondary clarification, (c) anion exchange membrane adsorbtion, (d) tangential flow filtration and (e) filtration. In more particularity, such steps comprise (a) clarifying the cell culture fluid by low-speed centrifugation, (b) further clarifying the supernatant by filtration through a 0.2 to 0.45 μm filter, (c) purifying the VSV filtered solution on an anion exchange membrane adsorber, (d) buffer exchanging and concentrating the VSV by tangential flow filtration (TFF) and (e) a final filtration of the VSV retentate through a 0.2 to 0.22 μm filter. In certain other embodiments, the purification process steps (a) through (e) above are performed at room temperature. As defined hereinafter, "room temperature" is a temperature or temperatures on or between 15° C. and 25° C. Thus, for example, a suitable temperature for performing the steps (a) through (e) includes a temperature of at least 15, 16, 17, 18, 19, 20, 21, 22, 23, 24 and including 25° C. or fractional temperatures therebetween. In one particular embodiment, the purification process steps (a) through (e) are performed at 20° C.

(a) Primary Clarification

In certain embodiments, the cell culture fluid of a mammalian cell culture infected with VSV is clarified by low-speed centrifugation (or alternatively, by depth filtration) and the VSV recovered in the supernatant, also referred to herein as "primary (or 1°) clarification" of the cell culture fluid. In certain embodiments, primary clarification of the cell culture fluid is conducted at room temperature.

The centrifugation methods and equipment used in the primary clarification of the cell culture fluid are well known to one of skill in the art. As defined hereinafter, "low-speed" centrifugation is a centrifugation speed below 10,000 rpm. In certain embodiments, the low-speed centrifugation speed used to clarify the cell culture fluid is a centrifugation speed within the range of 4,000×g (±100×g) to 8,000×g (±100×g). In certain other embodiments, the low-speed centrifugation speed used to clarify the cell culture fluid is a centrifugation speed of at least 4,000×g, 4,500×g, 5,000×g, 5,500×g, 6,000×g, 6,500×g, 7,000×g, 7,500×g or 8,000×g or rpms therebetween. In one particular embodiment, primary clarification of the cell culture fluid by low-speed centrifugation is at 6,238×g for thirty minutes at room temperature (Example 3, Table 2).

As stated above, in certain embodiments, the cell culture fluid of a mammalian cell culture infected with VSV is alternatively clarified (1°) by depth filtration (i.e., instead of low-speed centrifugation). Depth filtration can be used when low-speed centrifugation is omitted from primary clarification of step (a). Depth filtration (in contrast to surface filtration) generally refers to a "thick" filter that captures contaminants within its structure. Depth filtration materials and methods are well known to one of skill in the art. For example, the filter material is typically composed of a thick and fibrous cellulosic structure with inorganic filter aids such as diatomaceous earth particles embedded in the openings of the fibers. This filter material has a large internal surface area, which is key to particle capture and filter capacity. Such depth filtration modules contains pores of from 1.0 μm to 4.5 μm, including filter sizes of at least 1.0, 1.5, 2.0, 2.5, 3.0, 3.5, 4.0 and 4.5 μm, and fractional filter sizes therebetween. Exemplary depth filtration modules include, but are not limited to, Whatman® Polycap™ HD modules (Whatman Inc.; Florham Park, N.J.), Sartorius Sartoclear™ P modules (Sartorius Corp.; Edgewood, N.Y.) and Millipore® Millistak+® HC modules (Millipore; Billerica, Mass.). In one particular embodiment, the cell culture fluid is clarified via depth filtration (performed at room temperature) and the VSV is recovered in the filtrate (Example 3, Table 1).

(b) Secondary Clarification

After primary clarification via centrifugation (or depth filtration), the VSV supernatant (or filtrate) is further clarified (2°) by filtration, or microfiltration, through a 0.2 to 0.25 μm filter and recovery of the VSV in the filtered solution. In one particular embodiment, the microfiltration is performed at room temperature, as defined above. Filtration/Microfiltration media are available in a wide variety of materials and methods of manufacture, which are known to one of skill in the art. Exemplary microfiltration filter units include, but are not limited to, Millipore Millex®-GV filter units (Millipore; Billerica, Mass.), Millipore Millex®-GP filter units, Pall Supor® filter units (Pall Corp.; East Hills, N.Y.), Sartorius Sartobran™ filter units (Sartorius Corp.; Edgewood, N.Y.) and Sartorius Sartopore™ 2 filter units. In certain embodiments, these filtration units posses filters of a size between 0.2 to 0.45 μm. These filters include filters have pores of at least 0.2, 0.25, 0.3, 0.35, 0.4 and 0.45 μm and fractional pore sizes therebetween. In one particular embodiment, the filter is a 0.2 μm Sartorius Sartobran™ filter unit. The filtered VSV is recovered in the filtered solution.

(c) Anion Exchange Membrane Adsorbtion

Once the VSV product has been recovered by clarification (i.e., 1° and 2° described above), the VSV is further purified on an anion exchange membrane adsorber. Membrane adsorber materials are well known to one of skill in the art and available from vendors such as Sartorius Corp. (Edgewood, N.Y.), Pall Corp. (East Hills, N.Y.) and Sigma-Aldrich Corp. (St. Louis, Mo.). Exemplary anion exchange membrane adsorbers include, but are not limited to a Sartobind™ Q membrane adsorber (Sartorius Corp.) and a Mustang™ Q membrane adsorber (Pall Corp.). In one particular embodiment, the anion exchange membrane adsorber is a Pall Mustang™ Q membrane adsorber. In general, methods and buffers known from conventional ion exchange chromatography can be directly applied to membrane adsorber chromatography, which are known to one of skill in the art. In certain embodiments, the anion exchange membrane adsorber chromatography is performed at room temperature, as defined above.

Thus, in certain embodiments, VSV is purified via an anion exchange membrane adsorber, wherein the VSV filtered solution from the secondary clarification is loaded onto the anion exchange membrane adsorber equilibrated with a first pH buffered salt solution (also referred to as an "equilibration buffer" or VSV "binding buffer"). The VSV is eluted from the anion exchange membrane adsorber with a second pH buffered salt solution ("the elution buffer") and the eluted VSV fractions are recovered (e.g., see Example 6 below)

In certain embodiments, the first pH buffered salt solution or equilibration buffer is an NaCl or KCL salt solution. The NaCl or KCl is present in solution at an ionic strength between about at least 0.1 M to about 0.4 M. Thus the ionic strengths of the salts include at least 0.1, 0.2, 0.3 and 0.4 M including fractional ionic strengths therebetween. In one particular embodiment, the salt is NaCl and the ionic strength of the NaCl solution is 0.3M. The buffer solution may be a phosphate buffer, a N-2-Hydroxyethylpiperazine-N'-2-ethanesulfonic acid (HEPES) buffer or a Tris(hydroxymethyl)aminomethane (TRIS) buffer. These buffers in certain embodiments have a pH between about 6.0 to about 8.0, i.e., a pH of at least 6.0, 6.2, 6.4, 6.6, 6.8, 7.0, 7.2, 7.4, 7.6, 7.8, and 8.0 or pH numbers therebetween. In one particular embodiment, the first pH buffered salt solution has a pH of 7.5. In yet other embodiments, the first buffer of the anion exchange membrane adsorption step has a pKa between 6.0 to 8.5, i.e., a pKa of at least 6.0, 6.2, 6.4, 6.6, 6.8, 7.0, 7.2, 7.4, 7.6, 7.8, 8.0, 8.2, 8.4 and 8.5 or pKa numbers therebetween.

In particular embodiments, the equilibration buffer further comprises about 1% sucrose to about 5% sucrose. In certain embodiments, the equilibration buffer comprises about 1% sucrose. In one particular embodiment, the sucrose concentration is 2%. In another embodiment the buffer comprises about 3% sucrose. In another embodiment the buffer comprises about 4% sucrose. In another embodiment the buffer comprises about 5% sucrose. Still other percentages of sucrose concentration between the above-specified integers are useful.

The second pH buffered salt solution (the "elution buffer") may also comprise the same buffering components as the first (equilibration) buffer. In certain embodiments, the second pH buffered salt solution or equilibration buffer is an NaCl or KCL salt solution. In one particular embodiment, the salt in the second pH buffered salt solution is NaCl. The NaCl or KCl is present in solution at an ionic strength between about at least 0.1 M to about 0.4 M. Thus the ionic strengths of the salts include at least 0.1, 0.2, 0.3 and 0.4 M including fractional ionic strengths therebetween. In one particular embodiment, the salt is NaCl and the ionic strength of the NaCl solution is 0.3M. The buffer solution may be a phosphate buffer, a N-2-Hydroxyethylpiperazine-N'-2-ethanesulfonic acid (HEPES) buffer or a Tris(hydroxymethyl)aminomethane (TRIS) buffer. These buffers in certain embodiments have a pH between about 6.0 to about 8.0, i.e., a pH of at least 6.0, 6.2, 6.4, 6.6, 6.8, 7.0, 7.2, 7.4, 7.6, 7.8, and 8.0 or pH numbers therebetween. In one particular embodiment, the second pH buffered salt solution has a pH of 7.5. In yet other embodiments, the second buffer of the anion exchange membrane adsorption step has a pKa between 6.0 to 8.5, i.e., a pKa of at least 6.0, 6.2, 6.4, 6.6, 6.8, 7.0, 7.2, 7.4, 7.6, 7.8, 8.0, 8.2, 8.4 and 8.5 or pKa numbers therebetween.

In particular embodiments, the elution buffer further comprises about 1% sucrose to about 5% sucrose. In certain embodiments, the elution buffer comprises about 1% sucrose. In one particular embodiment, the sucrose concentration is 2%. In another embodiment the buffer comprises about 3% sucrose. In another embodiment the buffer comprises about 4% sucrose. In another embodiment the buffer comprises about 5% sucrose. Still other percentages of sucrose concentration between the above-specified integers are useful.

To elute the VSV from the membrane, the salt (NaCl or KCl) concentration (ionic strength) of the elution buffer is increased by linear gradient or in a single step elution process (Example 6). Both steps are equally effective at eluting VSV from the anion exchange membrane adsorber. In one particular embodiment, the ionic strength of the NaCl in the second pH buffered salt solution is between 0.5 M to 0.75 M. In another particular embodiment, the ionic strength of the NaCl in the second pH buffered salt solution is 0.6 M. In yet other embodiments, the ionic strength of the NaCl in the second pH buffered salt solution is 0.75 M.

In certain other embodiments, the second pH buffered salt solution has an elution flow rate of 10 capsule volumes/minute (CV/minute) to 30 CV/minute. Thus, in certain embodiments, the elution flow rate is at least 10, 12, 14, 16, 18, 20, 22, 24, 26, 28 to 30 CV/minute, or rates therebetween. In a particular embodiment, the elution flow rate is 20 CV/minute.

In certain other embodiments, the ionic strength of the NaCl in the second pH buffered salt solution is linearly increased from 0.001 M to 0.75 M at an elution flow rate of 10 CV/minute to 30 CV/minute as described above. In one particular embodiment, the linear elution gradient flow rate is 20 CV/minute.

(d) Tangential Flow Filtration (TFF)

Following VSV purification by anion exchange membrane adsorber chromatography, the VSV is further purified by tangential flow filtration (TFF). In general, TFF is a pressure driven process that uses a membrane(s) to separate components in a liquid solution (or suspension), wherein a fluid (the feed flow) is pumped tangentially along the surface of the membrane and an applied pressure serves to force a "portion" of the fluid through the membrane to the filtrate side (of the membrane). In certain embodiments TFF is performed at room temperature. In this process, the buffer is exchanged and the VSV is concentrated. In one embodiment, the TFF comprises concentrating the VSV recovered from the anion exchange membrane adsorption step at least 5 times, followed by at least one buffer exchange. In another embodiment, the TFF comprises concentrating the VSV recovered from the anion exchange membrane adsorption step at least five to ten times, followed by at least five, or at least six, buffer exchanges. Still other embodiments involve at least two, at least three, at least four, at least five, or at least six buffer exchanges following the concentration of VSV recovered from the anion exchange membrane adsorption step.

TFF materials (e.g., hollow fiber, spiral-wound, flat plate) and methods (e.g., ultrafiltration (UF), diafiltration (DF), microfiltration) are well known to one of skill in the art. In certain embodiments, the TFF membrane has a 300 kDa molecular weight cutoff. In certain embodiments, the TFF membrane has a 350, 400, 450, 500, 550, 600, 650 or 700 kDa molecular weight cutoff. In yet another embodiment, the TFF membrane has a 750 kDa molecular weight cutoff. In one embodiment, the TFF membrane is a hollow fiber membrane module.

In one particular embodiment, the buffer used in the buffer exchange of the TFF is a phosphate buffer, HEPES buffer or TRIS buffer as described above. However, the buffer in certain embodiments has a concentration of 5 mM to 15 mM, including concentrations of at least 5 mM, 6 mM, 7 mM, 8 mM, 9 mM, 10 mM, 11 mM, 12 mM, 13 mM, 14 mM and 15 mM, and further including mM concentrations therebetween. In certain embodiments, the buffer has a pH of between about 7.2 to 7.5. Thus in one embodiment the buffer has a pH of 7.2, 7.3, 7.4 or 7.5 or fractional pH values therebetween. In another embodiment, the buffer exchange buffer further comprises 0.10 M to 0.20 M NaCl and 3.5% to 4.5% sucrose.

In one particular embodiment (see Example 7), VSV fractions from the anion exchange membrane adsorber purification are pooled, and the pooled solution is concentrated and the buffer exchanged by TFF using a hollow fiber TFF membrane cartridge with a molecular weight cut-off of 750 kDa (GE Healthcare Bio-Sciences Corp.; Piscataway, N.J.).

(e) Filtration

The last process step in the purification is a final microfiltration of the VSV retentate from the TFF, wherein the retentate is filtered through a 0.2 to 0.25 μm filter, as described above for secondary clarification via microfiltration and further described below in Example 7. For example, such a filtration set may employ a filter of size 0.20, 0.21, 0.22, 0.23, 0.24 or 0.25 μm, or fractional sizes therebetween.

The purification of VSV according to the novel processes described herein is described in detail in the Examples below, which description includes primary (Example 3) and secondary (Example 4) clarification of the culture fluid, comprising low-speed centrifugation (or depth filtration) and 0.2-0.45 μm filtration, respectively. Following the clarification steps, VSV is further purified sequentially by an anion exchange membrane adsorber (Example 6); tangential flow filtration; ultrafiltration and diafiltration (Example 7) and 0.2-0.22 μm filtration (Example 7). Four large scale (4.5 L) VSV cell culture runs (scale-up runs) were also purified according to the novel process described herein (Example 8), wherein greater than 99.9% and 99.8% of the protein impurities (Table 11) and DNA (Table 13), respectively, were removed during purification.

III. Recombinant Vesicular Stomatitis Virus

As described herein, VSV of improved purity are obtained from mammalian cell culture by employing the novel purification methods described above. By "improved purity" is meant that the purified VSV is at least 90.0% free of cell culture protein and nucleic acid contaminants. In other embodiments, the VSV of improved purity is 99.0% free of cell culture protein and nucleic acid contaminants. In one particular embodiment, the VSV of improved purity is 99.8% free of cell culture protein and nucleic acid contaminants.

In particular embodiments, the vesicular stomatitis virus (VSV) purified from cell culture fluid of a mammalian cell culture by the process described above is a recombinant or genetically modified VSV. Methods of producing recombinant RNA viruses, such as VSV, are well known and referred to in the art as "rescue" or "reverse genetics" methods. Exemplary rescue methods for VSV include, but are not limited to, the methods described in U.S. Pat. No. 6,033,886 and U.S. Pat. No. 6,168,943, each incorporated herein by reference. Additional techniques for conducting rescue of viruses, such as VSV, are described in U.S. Pat. No. 6,673,572 and WO 2004/113517, which are hereby incorporated by reference.

The VSV of improved purity, which is purified and isolated according to the novel purification processes described herein, may be a VSV of a specified serotype. In certain embodiments, the purified VSV is an Indiana serotype, a New Jersey serotype, a San Juan serotype, an Isfahan serotype, a Glasgow serotype or a Chandipura serotype. In certain embodiments the VSV may contain sequences from more than one such serotype.

VSV vectors (and immunogenic compositions thereof) purified according to the processes described herein often comprise one or more attenuating mutations within the VSV genome. In certain embodiments, the purified VSV has a genomic sequence comprising at least one mutation which attenuates the pathogenicity of VSV. In other embodiments, the purified VSV has a genomic sequence comprising at least two mutations which attenuate the pathogenicity of VSV. For example, an attenuated VSV comprises two or more known attenuating mutations, such as the attenuating mutations set forth in International Application No. PCT/US2005/011499 (International Publication No. WO 2005/098009), incorporated herein by reference. For example, known VSV attenuating mutations include, but are not limited to, gene shuffling mutations (including gene shuffles of the VSV genes forming the VSV genome and designated N, P, M, G and L), G protein insertional mutations, G protein truncation mutations, temperature sensitive (ts) mutations (and other point mutations), non-cytopathic M gene mutations, G-stem mutations, ambisense RNA mutations and gene deletion mutations, each of which are set forth in detail in International Publication No. WO 2005/098009. Thus, in certain embodiments, the purified VSV comprises one or more attenuating mutations, including, without limitation, a temperature-sensitive (ts) mutation, a point mutation, a gene shuffling mutation, a G-stem mutation, a non-cytopathic M gene mutation, an ambisense RNA mutation, a truncated G gene mutation, a G gene insertion mutation and a gene deletion mutation.

In certain embodiments, a VSV purified by the purification process described herein has a genomic sequence comprising one or more foreign or heterologous (or foreign) polynucleotide sequences, such as a foreign RNA open reading frame (ORF). The heterologous polynucleotide sequences can vary as desired, and include, but are not limited to, a gene encoding a cytokine (such as an interleukin), a gene encoding T-helper epitope, a gene encoding a CTL epitope, a gene encoding an adjuvant and a gene encoding a co-factor, a gene encoding a restriction marker, a gene encoding a therapeutic protein or a protein of a different microbial pathogen (e.g. virus, bacterium, parasite or fungus), especially proteins capable of eliciting desirable immune responses. For example, the heterologous polynucleotide sequences encoding a protein of a different microbial pathogen may be one or more of a HIV gene, a HTLV gene, a SIV gene, a RSV gene, a PIV gene, a HSV gene, a CMV gene, an Epstein-Barr virus gene, a Varicella-Zoster virus gene, a mumps virus gene, a measles virus gene, an influenza virus gene, a poliovirus gene, a rhinovirus gene, a hepatitis A virus gene, a hepatitis B virus gene, a hepatitis C virus gene, a Norwalk virus gene, a togavirus gene, an alphavirus gene, a rubella virus gene, a rabies virus gene, a Marburg virus gene, an Ebola virus gene, a papilloma virus gene, a polyoma virus gene, a metapneumovirus gene, a coronavirus gene, a *Vibrio cholerae* gene, a *Streptococcus pneumoniae* gene, *Streptococcus pyogenes* gene, a *Helicobacter pylori* gene, a *Streptococcus agalactiae* gene, a *Neisseria meningitidis* gene, a *Neisseria gonorrheae* gene, a *Corynebacteria diphtheriae* gene, a *Clostridium tetani* gene, a *Bordetella pertussis* gene, a *Haemophilus* gene, a *Chlamydia* gene, and a *Escherichia coli* gene. In certain embodiments, the purified VSV comprises an HIV gene sequence, wherein the HIV sequence is selected from the group consisting of gag, env, pol, vif, nef, tat, vpr, rev or vpu. In one specific embodiment, the HIV gene is gag or env.

In certain other embodiments, the purified VSV contains both at least one attenuating mutation and at least one heterologous ORF as described above. For example, the VSV immunogenic composition (i.e., $VSV_{IN}$ $N4CT_9$-gag1) purified according to the novel processes, and exemplified in Section V below (Examples 2-8), is a recombinant VSV comprising two attenuating mutations and an ORF encoding the HIV-1 gag protein.

In other embodiments, the VSV purified according to the novel processes described herein encodes the HIV gag gene, wherein the gag gene is inserted into the VSV genome at position one (3'-$gag_1$-NPMGL-5'), position two (3'-N-$gag_2$-PMGL-5'), position three (3'-NP-$gag_3$-MGL-5'), position four (3'-NPM-$gag_4$-GL-5'), position five (3'-NPMG-$gag_5$-L-5') or position six (3'-NPMGL-$gag_6$-5'). In other embodiments, the VSV purified according to the novel processes described herein encodes the HIV env gene, wherein the env gene is inserted into the VSV genome at position one (3'-$env_1$-NPMGL-5'), position two (3'-N-$env_2$-PMGL-5'), position three (3'-NP-$env_3$-MGL-5'), position four (3'-NPM-$env_4$-GL-5'), position five (3'-NPMG-$env_5$-L-5') or position six (3'-NPMGL-$env_6$-5').

One of skill in the art would understand from the above description that a variety of recombinant VSV may be designed and purified according to the methods and processes described above.

IV. Immunogenic and Pharmaceutical Compositions

In certain embodiments, the immunogenic compositions comprise an immunogenic dose of a genetically modified VSV purified according to the purification processes described herein. For example, in certain embodiments, an immunogenic composition comprises a recombinant VSV purified according to the purification processes described herein, wherein the VSV comprises one or more foreign RNA sequences inserted into or replacing a region of the VSV genome non-essential for replication. Any of the embodiments of recombinant VSV described in Section III above can be employed in these immunogenic compositions. Thus, in certain embodiments, a purified VSV immunogenic composition is formulated for administration to a mammalian subject (e.g., a human).

Such compositions typically comprise the purified VSV vector and a pharmaceutically acceptable carrier. As used hereinafter the language “pharmaceutically acceptable carrier” is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the VSV vector, such media are used in the immunogenic compositions described herein. Supplementary active compounds may also be incorporated into the compositions.

Thus, a VSV immunogenic composition described herein is formulated to be compatible with its intended route of administration. Examples of routes of administration include parenteral (e.g., intravenous, intradermal, subcutaneous, intramuscular, intraperitoneal) and mucosal (e.g., oral, rectal, intranasal, buccal, vaginal, respiratory). Solutions or suspensions used for parenteral, intradermal, or subcutaneous application include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The pH is adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier is a solvent or dispersion medium containing, for example, water, ethanol, polyol (e.g., glycerol, propylene glycol, and liquid polyethylene glycol, and the like), and suitable mixtures thereof. The proper fluidity is maintained, for example, by the use of a coating such as lecithin, by the maintenance of the required particle size in the case of dispersion and by the use of surfactants. Prevention of the action of microorganisms is achieved by various antibacterial and antifungal agents, for example, parabens, chlorobutanol, phenol, ascorbic acid, and the like. In many cases, it is preferable to include isotonic agents, for example, sugars, polyalcohols such as mannitol, sorbitol, sodium chloride in the composition. Prolonged absorption of the injectable compositions is brought about by including in the composition an agent which delays absorption, for example, aluminum monostearate and gelatin.

Sterile injectable solutions are prepared by incorporating the VSV vector in the required amount (or dose) in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

For administration by inhalation, the compounds are delivered in the form of an aerosol spray from pressured container or dispenser which contains a suitable propellant (e.g., a gas such as carbon dioxide, or a nebulizer). Systemic administration can also be by mucosal or transdermal means. For mucosal or transdermal administration, penetrants appropriate to the barrier to be permeated are used in the formulation. Such penetrants are generally known in the art, and include, for example, for mucosal administration, detergents, bile salts, and fusidic acid derivatives. Mucosal administration is accomplished through the use of nasal sprays or suppositories. The compounds are also prepared in the form of suppositories (e.g., with conventional suppository bases such as cocoa butter and other glycerides) or retention enemas for rectal delivery.

In certain embodiments, it is advantageous to formulate oral or parenteral compositions in dosage unit form for ease of administration and uniformity of dosage. Dosage unit form as used hereinafter refers to physically discrete units suited as unitary dosages for the subject to be treated; each unit containing a predetermined quantity of active compound calculated to produce the desired therapeutic effect in association with the required pharmaceutical carrier. The specification for the dosage unit forms described herein are dictated by and directly dependent on the unique characteristics of the active compound and the particular therapeutic effect to be achieved, and the limitations inherent in the art of compounding such an active compound for the treatment of individuals.

V. Examples

The following examples were carried out using standard techniques, which are well known and routine to those of skill in the art, except where otherwise described in detail. The following examples are presented for illustrative purposes, and should not be construed in any way limiting the scope of the compositions and processes described herein. Examples 1 and 2 relate to all three VSV constructs exemplified. Examples 3-9 refer specifically to the construct $VSV_{IN}$ $N4CT_9$-gag1. Examples 10-11 refer specifically to the construct $VSV_{IN}$ N4$CT_1$-gag1. Example 12 refers specifically to the construct $VSV_{NJ}$ N4$CT_1$-gag1.

A recombinant VSV (Indiana serotype; $rVSV_{IN}$) purified in the following examples comprises the HIV gag gene at the first position of the VSV genome (gag1), and the N gene shuffled to the fourth position of the VSV genome (N4). In one construct, the VSV has a G gene having a truncated cytoplasmic tail ("$CT_9$"), wherein this construct was designated "$VSV_{IN}$ N4$CT_9$-gag1". In another construct, the VSV has a G gene having a truncated cytoplasmic tail ("$CT_1$"), wherein this construct was designated "$VSV_{IN}$ N4$CT_1$-gag1". In other examples, a recombinant VSV (New Jersey serotype; $rVSV_{NJ}$) purified in the following examples comprises the HIV gag gene at the first position of the VSV genome (gag1), the N gene shuffled to the fourth position of the VSV genome (N4), and a G gene having a truncated cytoplasmic tail ("$CT_1$"), wherein this construct was designated "$VSV_{NJ}$ N4$CT_1$-gag1". These constructs and mutations are defined in detail in International Publication No. WO 2005/098009, incorporated by reference herein.

However, the novel purification processes described herein are in no way limited to a specific rVSV construct or serotype (e.g., Indiana, New Jersey, etc.), and as such, these purification processes include the purification of VSV constructs comprising wild-type genomic sequences, attenuated genomic sequences, "foreign" nucleic acid sequences, or any combination thereof (e.g., see Section III above for an overview of such VSV constructs). Furthermore, methods of producing "recombinant" RNA viruses are well known and referred to in the art as "rescue" or "reverse genetics" methods. Exemplary rescue methods for recombinant VSV are described in above in Section III.

The following examples describe the purification of rVSV (as exemplified with the $VSV_{IN}$ N4$CT_9$-gag1, the $VSV_{IN}$ N4$CT_1$-gag1 or the $VSV_{NJ}$N4$CT_1$-gag1 construct) from Vero cells. However, the VSV purification processes set forth herein are equally applicable for purifying VSV from any suitable mammalian cell culture, including but not limited to human embryonic kidney (HEK) cells (e.g., HEK 293 cells), Chinese hamster ovary (CHO) cells and baby hamster kidney (BHK) cells.

Example 1

Protein, DNA and VSV Potency Assays

The following assays were utilized to assess the purification processes described hereinafter in Examples 2-12.

Total Protein Concentration. Total protein concentration was determined using the bicinchoninic acid (BCA) assay (Bio-Rad Laboratories Inc.; Hercules, Calif.) with bovine serum album (BSA) as a protein standard.

SDS-PAGE and Western Blot Analysis. For protein separation and detection, VSV samples were mixed with a Tri-glycine sample buffer at a 1:1 (for $VSV_{IN}$ N4$CT_9$-gag1 construct) or 3:1 (for $VSV_{IN}$ N4$CT_1$-gag1 construct) ratio, boiled for ten minutes at 100° C., and resolved by 4-20% Tris-glycine sodium dodecyl sulfate-polyacrylamide gel electrophoresis (SDS-PAGE), followed by double-staining with silver stain (Wako Chemicals USA, Inc.; Richmond, Va.) and colloidal Coomassie® Blue stain (Invitrogen Corp.; Carlsbad, Calif.). The sensitivity of the double staining made it possible to easily detect high molecular weight impurities in the VSV samples.

After gel electrophoresis, the proteins were electrophoretically transferred to a nitrocellulose membrane (Amersham Biosciences Corp.; Piscataway, N.J.). After blocking for one hour in Tri-buffered saline (TBS) containing 3% BSA, the membrane was incubated in an antibody solution (1% BSA in TBS with 0.05% Tween-20 (TTBS) containing rabbit anti-VSV polyclonal antibodies produced from BHK cells, 1:1000 v/v), and probed with a goat anti-rabbit antibody conjugated with Horseradish peroxidase (HRP, 1:1000 (v/v)) (Bio-Rad Laboratories Inc.; Hercules, Calif.). After washing with TTBS and TBS, HRP color development reagents (Bio-Rad Laboratories Inc.; Hercules, Calif.) were added for detection, and the reaction was quenched with distilled water. The stained gel and developed membrane were captured via an AlphaImager® imaging system (Alpha Innotech Corp.; San Leandro, Calif.) with AlphaEaseFC® software.

Size-Exclusion High Performance Liquid Chromatography (SE-HPLC). A size exclusion-HPLC protocol was developed for rapidly separating VSV from impurity proteins, thereby permitting a qualitative analysis of the VSV purification process. Thus, "in-process" VSV samples (100 μL) and purified bulk concentrate VSV (100 μL) were loaded onto an analytical size exclusion column (TSK-Gel PW column G6000$PW_{XL}$, particle size 17μ, pore size 1000 Å) (Tosho Biosciences LLC.; Montgomeryville, Pa.), equilibrated with PBS buffer (without $Ca^{2+}$ or $Mg^{2+}$) and developed at a flow rate of one mL per minute. The system was powered with an Agilent 1100™ solvent delivery system controlled with ChemStation™ software (Agilent Technologies Inc.; Palo Alto, Calif.). UV spectra were collected via photodiode assay detector and chromatograms were obtained by monitoring the UV absorbance at 215 nm.

VSV Potency Assays. VSV potency was quantified via two different methods, a traditional plaque assay and an immunofluorescence plaque assay. For the traditional plaque assay, Vero cells in DMEM+10% FBS were seeded onto six-well plates at a concentration of $1\times10^6$ cells/well (with two mL cell culture/well) and incubated overnight at 37° C. Cells were checked the following day to ensure confluent monolayers had formed. Virus samples of unknown titer, along with positive and negative controls were serially diluted 1:10 to the expected titer ranges in DMEM+10 ml/L Sodium Pyruvate+0.5 ml/L Gentamicin. The positive control was a VSV standard of known titer. The negative control (or blank) contained media only. Cell media was aspirated from the six-well plates, then the diluted virus (0.5 ml virus solution/well) was added to the wells, in duplicate. Virus was adsorbed at room temperature for fifteen minutes, then incubated at 32° C. for thirty minutes. The plates were rocked by hand every five to ten minutes to keep cell monolayers moist. Agarose (at 50° C.) and DMEM (at 37° C., 10 ml/L Sodium Pyruvate and 0.5 ml/L Gentamycin) were combined in a 1:4 ratio to create an agar overlay media. Virus was aspirated from the plates, and 3 ml of overlay was added per well using a repeater pipette. Overlaid plates were cooled under a hood at room temperature, then transferred to 32° C. incubation for seventy-two hours or until plaques were clearly visible (approximately one mm in diameter or larger). Plaques were counted by holding plates up to a light source. Titers were determined for each sample using the resulting plaque counts and expressed in terms of plaque forming units (PFU) per ml.

The second assay (immunofluorescence plaque assay) was performed by infecting of Vero cell monolayers (in 48-well plates) with VSV. After twenty-four to thirty-six hours, the Vero Cells were fixed and first probed with a monoclonal antibody against either $VSV_{IN}$ or $VSV_{NJ}$, depending on the construct used, and then probed with a secondary antibody conjugated to a fluorescent dye. Infectious particles were quantified using fluorescence microscopy to detect fluorescent foci within the Vero cell monolayer. The fluorescent foci were counted and the titer of the sample was expressed as infectious units (IU) or plaque forming units (PFU) per mL.

Residual DNA Assay. Host cell DNA was tested and quantified using the PicoGreen® Quant-iT™ DNA microassay kit (Invitrogen Corp.; Carlsbad, Calif.). The microassay was performed according to the manufacturer's instruction using lambda DNA as the standard.

Example 2

Producing VSV in Vero Cell Culture

VSV experimental runs were produced in a 10-liter bioreactor, using Vero cell (African Monkey Kidney Cells) microcarrier cultures. The Vero cells used were obtained from a cGMP Master Cell Bank. Vero cells were grown on Cytodex™ I microcarriers (Amersham Biosciences Corp.; Piscataway, N.J.) at a density of 7.5 grams dry beads/liter. The working volume for the bioreactor culture was 5.5 to 6.5 liters. For inoculation, Vero cells were combined with Cytodex™ I microcarriers in a total volume of approximately 2 liters. The target seeding density of the culture was $5\times10^5$ cells/ml. A two-hour intermittent agitation cycle was performed at this reduced volume to promote cell attachment to the microcarriers. The culture was agitated for 5 minutes at 40 rpm, then allowed to settle for 20 minutes at zero rpm, for four complete cycles.

The culture was sampled following intermittent agitation, and if attachment was satisfactory, Virus Production Serum-Free Medium (VP-SFM) was added to the culture, up to the 5.5 or 6.5-liter working volume. Cells were grown to $2\text{-}4\times10^6$ cells/ml at 37° C. and 40 rpm. Air was constantly supplied to the overlay at 50 $cm^3$/minute. Carbon dioxide and oxygen were supplied to the overlay upon demand, at 50 $cm^3$/minute. When oxygen demand of the culture exceeded that provided by the overlay, oxygen was added to the culture through a scintered sparger at an initial rate of 6 $cm^3$/minute. The rate was increased manually as oxygen demand increased. Carbon dioxide (acidic) and 7.5% weight/volume Sodium Bicarbonate solution (basic) were used to control pH, using a culture set-point of pH 7.30. The culture underwent perfusion with fresh media at half a culture volume per day starting at approximately 48 hours of elapsed culture time. The infection of the Vero cells with rVSV occurred at 32° C. and a multiplicity of infection (MOI) of 0.01. To promote virus adsorption to the cells, a one-hour intermittent agitation cycle was performed immediately after addition of the virus to the bioreactor culture. The culture was agitated for six minutes at 40 rpm, then allowed to settle for twenty-four minutes at zero rpm, for two complete cycles. Following one hour of intermittent agitation, the remainder of the infection proceeded in batch mode at 40 rpm. The infected culture was sampled every 6-16 hours to observe cytopathic effect (CPE), count cells, and collect viral supernatant samples for growth kinetics determination.

The cell culture was harvested at approximately 44 hours post-infection for $VSV_{IN}N4CT_9$-gag1, at approximately 48 hours post-infection for $VSV_{IN}N4CT_1$-gag1, and at approximately 60 hours post-infection for $VSV_{NJ}N4CT_1$-gag1, by allowing the microcarriers to settle and collecting the culture fluid supernatant. For the latter construct, the cell culture fluid from two bioreactors was combined.

Example 3

VSV Purification Process: Primary Clarification of VSV Cell Culture Fluid for $VSV_{IN}N4CT_9$-gag1

After harvesting the cell culture from the bioreactor, cells/cell debris and other particulate impurities were removed in the process known as "product recovery". Because VSV was secreted from the Vero cells into the culture fluid, the VSV was recovered in the clarified culture fluid. Thus, VSV cell culture fluid supernatant (e.g., about 4.0-4.5 L from a 10 L bioreactor run) was clarified by either depth filtration or low-speed centrifugation.

Clarification via depth filtration was performed at room temperature and the VSV was recovered in the filtrate. The following depth filtration modules were tested: a Whatman® Polycap™ HD module (Whatman Inc.; Florham Park, N.J.), a Sartorius Sartoclear™ P module (Sartorius Corp.; Edgewood, N.Y.), a Millipore® Millistak+® HC module (Millipore; Billerica, Mass.) and a CUNO 05/60HP (CUNO Inc, a 3M® company, Meriden, Conn.). The depth filters were loaded with filtrate until the filter was saturated (approximately 100-500 ml of filtrate).

The clarification efficiency of the depth filtration modules was determined by a turbidity meter, while virus recovery was evaluated by viral plaque assay. Table 1 below summarizes the performance of different depth filters.

A high virus recovery can be achieved using Whatman Polycap HD 75. However, in large-scale production, low turbidity removal efficiency and low filter capacity were observed. Other filters from different vendors may be selected for use in the clarification process based upon an evaluation of their virus product recovery.

TABLE 1

CELL CULTURE CLARIFICATION PERFORMANCE OF DIFFERENT DEPTH FILTERS

| Filters | Filtrate Turbidity[1] | Turbidity Removal | Filter Capacity[2] | Titer Recovery |
|---|---|---|---|---|
| Millipore Co HC | 1.24 | 96.3% | >6.5 | 4.4% |
| Sartorius Sartoclear ™ P (1.5 μm) | 4.0 | 94.0% | >8.0 | 19.3% |
| Sartorius Sartoclear ™ P (4.0 μm) | 7.0 | 89.6% | >8.7 | 8.4% |
| Whatman PolyCap ™ HD75 | 13.8 | 79.4% | 1.25 | 82.0% |
| CUNO ™ 05/60HP | 6.4 | 96.9% | 9.0 | 33.9% |
| CUNO ™ 05/60HP | 6.7 | 85.4% | >32 | 41.1% |

Filtrate Turbidity[1] = NTU (Nephelometric Turbidity Unit)
Filter Capacity[2] = (L-culture/$ft^2$)

Clarification via low-speed centrifugation was performed at 6,238×g (5,000 rpm) for thirty minutes at room temperature on a Beckman centrifuge (5×1 L centrifugation bottles at a total volume of 4.5 L), wherein the VSV was recovered in the supernatant. As shown below in Table 2, higher turbidity removal efficiency, and an equivalent product recovery, was achieved by low-speed centrifugation as compared to depth filtration via the Whatman PolyCap™ HD75 module.

TABLE 2

COMPARISON OF PRIMARY CLARIFICATION OF CELL CULTURE FLUID BY LOW-SPEED CENTRIFUGATION AND DEPTH FILTRATION

| Clarification Method | Turbidity[1] | Turbidity Removal | Titer recovery |
|---|---|---|---|
| Centrifugation Experimental Run 1 | 8.45 | 74.4% | 67.8% |
| Whatman PolyCap ™ HD75 Experimental Run 1 | 18.13 | 45.5% | 66.6% |
| Centrifugation Experimental Run 2 | 9.03 | 86.5% | 55.7% |
| Whatman PolyCap ™ HD75 Experimental Run 2 | 13.8 | 79.4% | 82.0% |
| Centrifugation Experimental Run 3 | 10.13 | 77.6% | 68.3% |
| Centrifugation Experimental Run 4 | 10.80 | 85.5% | 77.0% |

Turbidity[1] = Filtrate or Supernatant Turbidity NTU

Example 4

VSV Purification Process: Secondary Clarification of VSV Cell Culture Fluid

After the primary clarification described above in Example 3, the supernatant (or filtrate) was further processed (secondary clarification) to reduce the turbidity level. Several sterile microfiltration filters (0.2 to 0.25 μm) were evaluated (Table 3), which included a Millipore Millex®-GV filter unit (Millipore; Billerica, Mass.), a Millipore Millex®-GP filter unit, a Pall Supor® filter unit (Pall Corp.; East Hills, N.Y.), a Sartorius Sartobran™ filter unit (Sartorius Corp.; Edgewood, N.Y.) and a Sartorius Sartopore™ 2 filter unit. The optimal filter should have limited (or no) VSV binding capacity, yet remove as much particulate contamination as possible.

VSV from pre-seed production was used as the feed (starting material) for the chosen microfiltration filters, which was spiked with 1× sucrose phosphate glutamate (SPG). The same feed was filtered following the protocol provided by the vendors. Since the amount of clarified cell culture material was limited, a syringe or disk filter was used instead of a large-scale filter. As shown in Table 3, the highest VSV titer recovery was achieved with the Pall Supor® and Sartorius Sartobran™ sterile filters.

TABLE 3

SECONDARY CLARIFICATION-FILTER SCREENING

| Filter Unit | Recovery* |
|---|---|
| Millipore Millex ®-GV | 66.13% |
| Millipore Millex ®-GP | 87.08% |
| Pall Acrodic ™ Supor ™ | 96.08% |
| Sartorius Sartobran ™ | 94.61% |
| Sartorius Sartopore ™ 2 | 82.84% |

Recovery*: 1 × SPG solution was added to feed solution. SPG is sucrose phosphate glutamate.

The secondary clarification of the VSV was further evaluated using the Sartorius Sartobran™ filter unit, the results of which are summarized below in Table 4.

TABLE 4

THE SECONDARY CLARIFICATION USING SARTORIUS SARTOBRAN ™ FILTER

| Sartobran ™ Filtration | Supernatant Turbidity[1] | Turbidity Removal | Titer recovery |
|---|---|---|---|
| Experiment 1 | 0.62* | 50.8% | 65.8% |
| Experiment 2 (w/ 1x SPG) | 4.45 | NA | 85.9% |
| Experiment 3 (w/ 1x SPG) | 6.27 | 54.6% | 110.0% |

Supernatant Turbidity[1] = NTU
0.62*: low filtrate turbidity is due to low feed turbidity
NA = Not Available;
SPG is sucrose phosphate glutamate The data in Table 4 show that the solution turbidity of Experiment 2 and Experiment 3 was further reduced with an acceptable level of recovery. It was also established in these experiments, that addition of 1×SPG to the feed solution (i.e., Experiment 2: 85.9% titer recovery and Experiment 3: 110% titer recovery) significantly improves the yield of VSV product recovery, relative to Experiment 1 which had no SPG added (65.8% titer recovery).

Example 5

VSV Purification Process: Column Chromatography

Following the secondary clarification step described in Example 4, purification of the VSV filtrate was tested/screened using several chromatographic resins. Since the VSV particle is large in size relative to contaminant proteins, only resins with a large pore size were evaluated, which included a UNOsphere™ Q anion exchange resin (Bio-Rad Laboratories Inc.), a UNOsphere™ S cation exchange resin (Bio-Rad Laboratories Inc.), a CHT ceramic hydroxyapatite type I resin (Bio-Rad Laboratories Inc.), CFT ceramic fluoroapatite type I resin (Bio-Rad Laboratories Inc.) and a CST I mixed mode resin (GE Healthcare). For comparison, two affinity resins were also evaluated, a Matrex™ Cellufine® Sulfate resin (Millipore) and a heparin sepharose resin (GE Healthcare). The experiments were performed on batch mode at room temperature. The samples from different wash and elution conditions were collected and assayed by SDS-PAGE and plaque assay.

It was observed in initial experiments with the UNOsphere™ Q anion exchange and UNOsphere™ S cation exchange resins, that VSV only bound to the UNOsphere™ Q anion exchange resin at neutral pH, indicating that VSV is negatively charged at neutral pH.

Evaluation of VSV purification on a Bio-Rad® UNOsphere™ Q Anion Exchange Resin. Clarified VSV was loaded onto a column packed with the UNOsphere™ Q resin. There was no distinguishable separation between VSV product and impurity proteins on the column, and a large portion of virus was still bound to the column even after elution with 2 M NaCl in 10 mM sodium phosphate buffer (data not shown).

Evaluation of VSV purification on a Bio-Rad® ceramic hydroxyapatite type I (CHT I) resin. VSV was efficiently adsorbed to the hydroxyapatite column. Some separation of VSV from contaminant proteins was observed by SDS-PAGE (data not shown), but a significant portion of the VSV remained bound on the column even after elution with 0.8 M sodium phosphate, pH 6.88, wherein the bound VSV was finally eluted off the column during a 1 M NaOH cleaning step.

In another experiment, 0.9 M potassium phosphate buffer was used as the elution buffer. Little separation between VSV and impurity proteins was achieved (data not shown). A large potion of VSV remained bound to the column and required 1.0 M NaOH to be eluted from the column. Similar results (i.e., poor VSV/contaminant protein separation and strong VSV binding to the resin) were observed with the ceramic fluoroapatite (CFT) type I resin and the CST I resin.

Evaluation of VSV purification on a Matrex® Cellufine™ Sulfate affinity resin. A clarified VSV feed solution was loaded into a pre-equilibrated (1.47 mM potassium phosphate, 8.06 mM sodium phosphate, 140 mM NaCl, pH 7.0) Cellufine™ Sulfate column (capsule volume (CV)=2 ml) at a flow rate of 3 ml/minute. The column was washed with 10 CV of equilibration buffer, which was phosphate buffered saline (1.47 mM potassium phosphate, 8.06 mM sodium phosphate, 140 mM NaCl, pH 7.0). The flow-through and wash were pooled. The adsorbed materials were then eluted with a 30 CV linear gradient to 10 mM sodium phosphate, 1.5 M NaCl, pH 7.0. The SDS-PAGE analysis showed that the separation between the impurity proteins and virus during the elution was not efficient and the VSV was observed in all the column elution fractions (data not shown). A large amount of the VSV also remained on the column. The total VSV product recovery (i.e., from all elution fractions collected; F3-F25) was only 45.2% (Table 5). Similar results (i.e., low VSV recovery) were observed with the heparin sepharose resin.

TABLE 5

VSV PURIFICATION ON A MATRIX CELLUFINE ® SULFATE COLUMN

| Samples | Volume (ml) | Virus titer (pfu/ml) | Virus titer (pfu) | Recovery |
|---|---|---|---|---|
| Feed | 22 | $1.39 \times 10^6$ | $3.06 \times 10^7$ | — |
| FT &W | 32 | $4.40 \times 10^4$ | $1.41 \times 10^6$ | 4.6% |
| F3-4 | 4 | $1.00 \times 10^4$ | $4.00 \times 10^4$ | 0.1% |
| F5 | 2 | $1.00 \times 10^5$ | $2.00 \times 10^5$ | 0.7% |
| F6-9 | 8 | $1.00 \times 10^5$ | $8.00 \times 10^5$ | 2.6% |
| F10-25 | 32 | $4.00 \times 10^5$ | $1.28 \times 10^7$ | 41.9% |
| | | | | Total 45.2% |

FT&W = Flow-through and wash pool
F3-F25 are elution fractions 3-25.

Example 6

VSV Purification Process: Anion Exchange Membrane Adsorber

As described above in Example 5, VSV recovery was relatively low when the filtrate from the secondary clarification step (i.e., 0.2 μm Sartobran™ filter) was purified with the UNOsphere™ Q resin, the UNOsphere™ S resin, the CHT I resin, the CFT I resin, the CST I resin, the Cellufine® resin or the heparin sepharose resin. Thus, purification of the VSV filtrate from Example 4 was further assessed using two anion exchange membrane adsorbers; a Sartobind™ Q membrane adsorber (Sartorius Corp.; Edgewood, N.Y.) and a Mustang™ Q membrane adsorber (Pall Corp.; East Hills, N.Y.).

VSV Purification on a Sartobind™ Q Membrane Adsorber

The VSV feed (starting material) for the membrane adsorber purification was retentate from a tangential flow filtration (TFF) separation (using a TFF membrane having a molecular weight cutoff of 750 kDa). The VSV retentate from the TFF separation (which comprises VSV and impurity/contaminant proteins and DNA) was then stored at either 4° C. or −70° C.

Initial Sartobind™ Q membrane adsorber studies were performed with the VSV retentate stored at 4° C., wherein 20 mM HEPES (pH 7.1) was used as the equilibration buffer and the retentate was adsorbed to the Sartobind™ Q membrane adsorber (2.1 ml membrane volume). The impurity proteins were eluted efficiently with an elution buffer of 20 mM HEPES (pH 7.1) and 1.0 M NaCl (data not shown). However, no VSV titer was recovered in any of the elution fractions. The buffer was switched from HEPES to sodium phosphate buffer, but similar results were observed (i.e., no VSV titer in fractions collected), even at high (1.5 M) NaCl concentrations in the phosphate elution buffer.

In contrast, when the VSV retentate stored at −70° C. was used as the starting material and adsorbed to the Sartobind™ Q membrane adsorber (equilibrated with 20 mM HEPES, pH 7.1), the VSV was observed in the elution fractions (elution buffer 20 mM HEPES and 1.0 M NaCl), wherein 74.2% of protein impurities were observed in the flow-through and wash pool based on BCA results (data not shown). The mass balance analysis for total protein is shown below in Table 6.

Using a linear elution gradient to 30% buffer B for the −70° C. VSV starting material, there were two major peaks observed in the chromatogram (data not shown). Buffer A (equilibration buffer) was 10 mM sodium phosphate (pH 7.0) and 0.3 M NaCl. Buffer B (elution buffer) was 10 mM sodium phosphate (pH 7.0) 2.0 M NaCl and 10 mM sucrose, wherein 30% B was approximately 0.81 M NaCl.

The first peak was VSV (fractions 4-10) with a relatively high purity. The second peak was host DNA contaminants (fractions 11-20). PicoGreen® assay results (data not shown) indicated that 97.3% of residual host DNA was removed with the Sartobind™ Q membrane adsorber. Thus, these data indicate that the Sartobind™ Q membrane adsorber provides an efficient way to remove host DNA contaminants from VSV product. However, results from a VSV titer assay (data not shown) indicated that VSV recovery from the Sartobind™ Q purification process was less than 30% by virus titer. A higher VSV recovery was observed using Mustang™ Q membrane adsorber with the same starting materials.

TABLE 6

TOTAL PROTEIN MASS BALANCE FOR SARTOBIND Q MEMBRANE ADSORBER

| In-process Samples | Volume (ml) | Total Protein (μg/ml) | Total Protein (μg) | Recovery |
|---|---|---|---|---|
| Feed | 15 | 115.8 | 1737 | 100% |
| FT &W | 32.5 | 39.68 | 1289.6 | 74.2% |
| F3 | 2 | 3.79 | 7.58 | 0.4% |
| F4-5 | 4 | 24.86 | 99.44 | 5.7% |
| F6-10 | 10 | 12.27 | 122.7 | 7.1% |
| F11-20 | 20 | 6.17 | 123.4 | 7.1% |
| F22-24 | 6 | 4.27 | 25.62 | 1.5% |
| F36 | 2 | 0 | 0 | 0.0% |
| F37 | 2 | 17.86 | 35.72 | 2.1% |
| F38-40 | 6 | 7.38 | 44.28 | 2.5% |
| | | | | Total 94.6% |

FT&W = Flow-through and wash pool
F3-F40 are elution fractions 3-40

VSV Purification on a Mustang™ Q Membrane Adsorber

The Mustang™ Q membrane adsorber was also investigated as a VSV purification means. Operating conditions for the Mustang™ Q adsorber were optimized and described below.

Figure 2A:
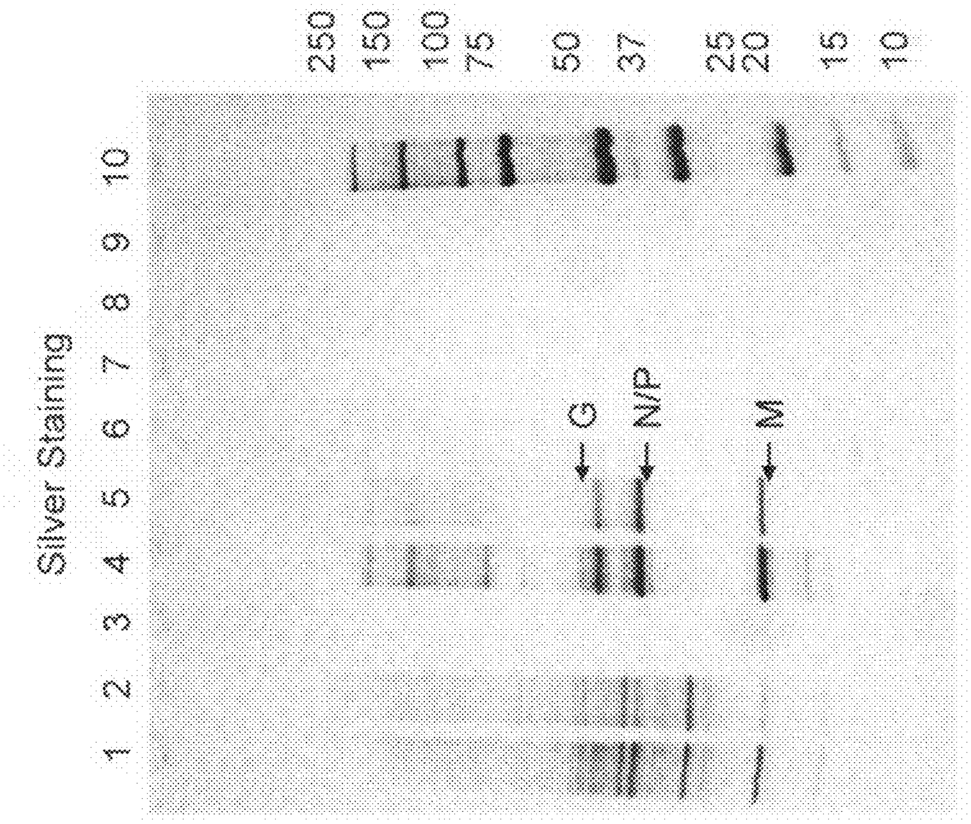
FIG. 2A is an electrophoretic gel showing the separation of VSV proteins by silver staining after purification on a Mustang™ Q membrane adsorber with 2% sucrose added to the elution buffer (10 mM sodium phosphate, 1.0 M NaCl). Lanes 1-10 are: (1) pre-centrifugation (cell culture), (2) feed, (3) flow-through and wash, (4) 5% buffer B (fractions 1-5), (5) 60% buffer B (fractions 6-7), (6) 60% buffer B (fractions 8-10), (7) 60% buffer B (fractions 11-25), (8) 100% buffer B (fractions 26-35), (9) column regeneration and (10) Bio-Rad® Precision Plus Protein™ standards. The flow rate for the Mustang™ Q was 3.5 ml/minute with a linear elution gradient. SDS-PAGE analysis was with a 4-20% Tris-Glycine gel and protein detection was by silver staining.
Figure 3B:
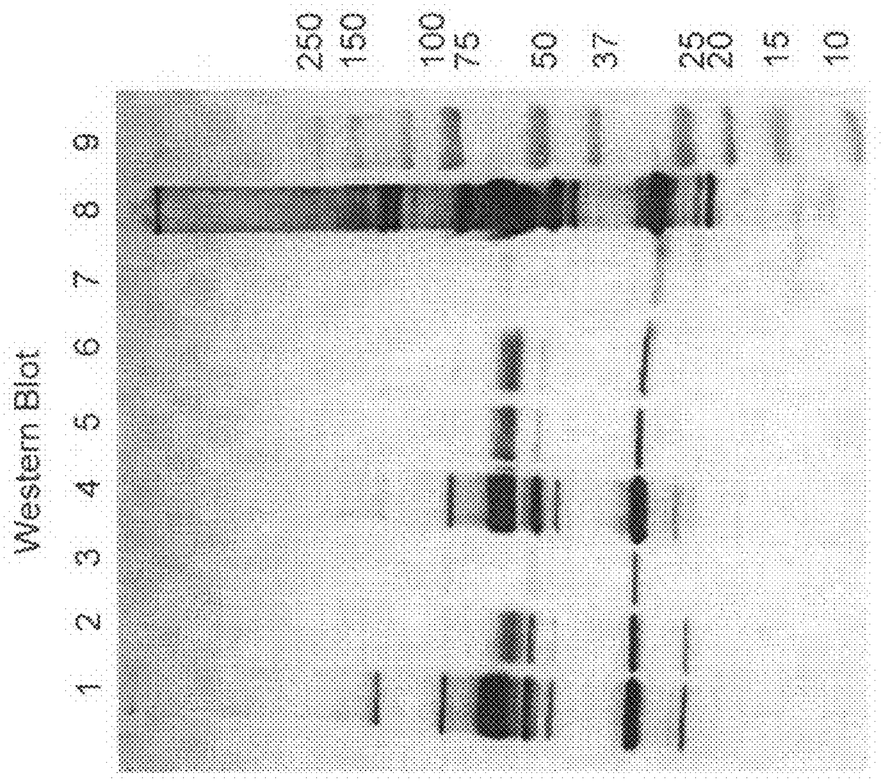
FIG. 3B is an electrophoretic gel showing the separation of VSV proteins by Western Blot after purification as described in FIG. 3A. The Western Blot detection was with anti-VSV polyclonal antibodies. Buffer B (also referred to as the "elution buffer") was 10 mM sodium phosphate (pH 7.0) and 1 M NaCl.
Figure 3A:
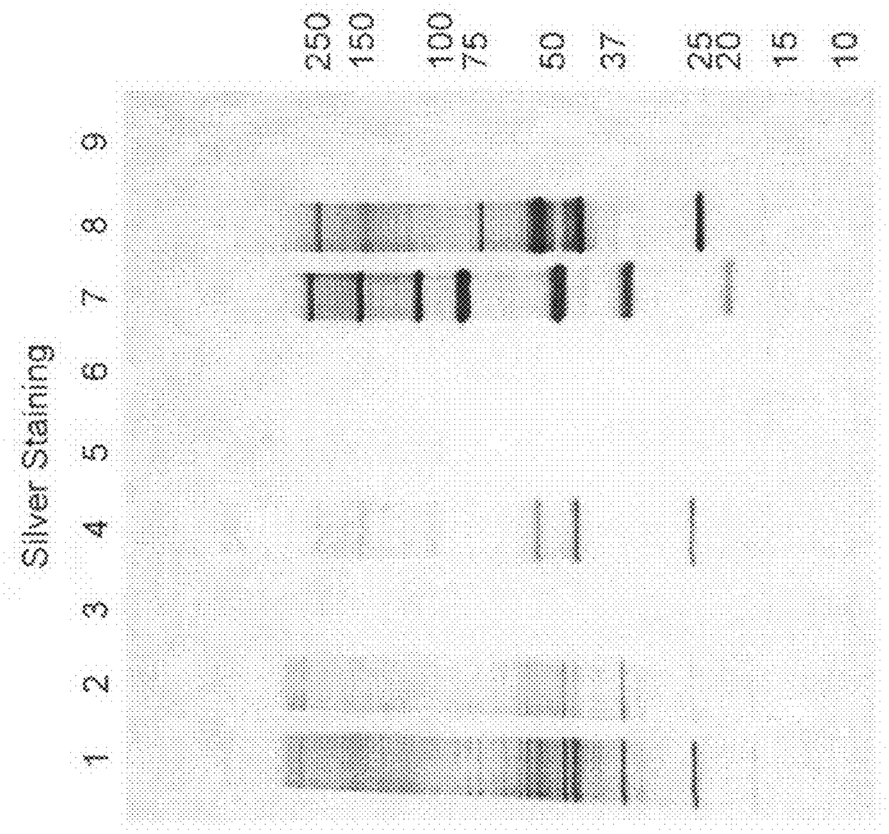
FIG. 3A is an electrophoretic gel showing the separation of VSV proteins by silver staining and Western blot after purification on a Mustang™ Q membrane adsorber without sucrose added to the elution buffer (10 mM sodium phosphate, 1.0 M NaCl). Lanes 1-9 are: (1) feed, (2) flow-through and wash, (3) 5% buffer B (fractions 1-5), (4) 60% B (fractions 6-11), (5) 60% buffer B (fractions 12-25), (6) 100% buffer B (fractions 26-35), (7) Bio-Rad® Precision Plus Protein™ standards, (8) VSV standard (i.e., sucrose gradient purified VSV) and (9) column regeneration pool. The flow rate for the Mustang™ Q was 3.5 ml/minute (10 CV/minute) with a step elution gradient. SDS-PAGE analysis was with a 4-20% Tris-Glycine gel and protein detection was by silver staining.

Sucrose improves recovery yield of VSV eluted from Mustang™ Q Membrane. An initial observation when optimizing the conditions for the Mustang™ Q, was the importance of including sucrose in the chromatographic buffers. For example, side-by-side purification experiments were performed with buffer formulated with sucrose (FIGS. 2A and 2B) and without sucrose (FIGS. 3A and 3B). The following chromatographic buffers were used: Buffer A (equilibration buffer) was 10 mM sodium phosphate (pH 7.0) and 300 mM NaCl. Buffer B (elution buffer) was 10 mM sodium phosphate (pH 7.0), 1 M NaCl, with and without (i.e., +/−2% sucrose).

In both experiments (i.e., +/−2% sucrose), a high purity VSV product was obtained. Plaque assays (data not shown) indicated VSV recovery was significantly higher (32.8% vs. 19.0%) when sucrose was included in the buffer.

Buffer pH and VSV binding to Mustang™ Q Membrane. Three different buffer pH ranges (pH 6.5, 7.0 and 7.5) were evaluated to determine the optimal buffer pH for VSV binding to the Mustang™ Q membrane. In these experiments, conditioned fresh cell culture after clarification was loaded onto a Mustang™ Q membrane equilibrated with either 10 mM sodium phosphate buffer at pH 6.5, 10 mM sodium phosphate buffer at pH 7.0 or 10 mM sodium phosphate buffer at pH 7.5 (each buffer also comprised 300 mM NaCl and 2% sucrose).

The VSV was eluted from the membrane by step elution (elution buffer: 10 mM sodium phosphate (pH 6.5, 7.0 or 7.5), 720 mM NaCl and 2% sucrose) at a flow rate of 3.5 ml per minute (10 CV/min). The purity of the VSV eluted from the Mustang™ Q (determined by SDS-PAGE and Western Blot; data not shown) was comparable for each of the buffer pH's tested. However, at pH 6.5, a significant amount of the VSV was dispersed in the flow-through, wash and elution steps during the chromatographic process, and as such, a lower VSV titer recovery was observed in the elution pool at this pH (see Table 7).

TABLE 7

VSV PROCESS RECOVERY AT DIFFERENT BINDING PH CONDITIONS

| Binding pH | VSV recovery (titer assay) |
|---|---|
| 6.5 | 15% |
| 7.0 | 33% |
| 7.5 | 28% |

Ionic Strength and VSV Binding to Mustang™ Q Membrane. Two different NaCl concentrations (0.15 M NaCl and 0.3 M NaCl) in 10 mM sodium phosphate binding (equilibration) buffer were tested in VSV adsorption to Mustang™ Q membrane. Better separation between the VSV and impurity proteins was observed at 0.3 M NaCl. For example, when 0.3 M NaCl was used in sodium phosphate binding buffer, the high molecular weight contaminants were removed in flow-through pool, wherein the VSV remained bound to the membrane (data not shown).

Ionic Strength and VSV Elution from the Mustang™ Q Membrane. The elution buffer (Buffer B) ionic strength (i.e., the NaCl concentration in the elution buffer) was determined by linear gradient elution, wherein the concentration of the elution buffer (Buffer B) was increased from 0% to 60% in 30 CV at a flow rate of 3.5 ml/minute. The equilibration buffer (Buffer A) was 10 mM sodium phosphate, pH 7.1, 300 mM NaCl and the elution buffer (Buffer B) was 10 mM sodium phosphate, pH 7.1, 2 M NaCl, 10 mM sucrose. It was observed from the chromatogram (data not shown), that a NaCl concentration of 0.6 M was required to elute 73.3% VSV from the Mustang™ Q membrane adsorber.

Linear Gradient Elution vs. Single Step Elution. A high quality VSV product was obtained from both a linear gradient elution (described above) and a "single step" elution strategy (data not shown). The linear gradient elution process comprises an equilibration buffer (Buffer A; e.g., 10 mM sodium phosphate, pH 7.1, 300 mM NaCl) and an elution buffer (Buffer B; e.g., 10 mM sodium phosphate, pH 7.1, 2 M NaCl, 10 mM sucrose). In contrast to the linear gradient elution, the single step elution process elutes the VSV from the membrane adsorber by instantaneously adding Buffer B at a specific final salt concentration (e.g., instantaneously adding Buffer B at a final NaCl concentration of 0.6 M). The single step elution process removed greater than 99% of the impurity proteins (BCA assay; data not shown), wherein 70-95% of the VSV was recovered in the eluted fractions (plaque assay; data not shown). Thus, the single step elution process will be used herein, since a high VSV titer was obtained using this simple one step elution strategy.

Operating Flow Rate. Two different flow rates were investigated, i.e., 10 capsule volumes (CV)/minute and 20 CV/minute. No change in purification process performance was observed at either flow rate.

Benzonase® Treatment. Benzonase® Nuclease is a genetically engineered endonuclease. It degrades all forms of DNA and RNA (single stranded, double stranded, linear and circular) while having no proteolytic activity. It is effective over a wide range of conditions, with high specific activity. Thus, Benzonase® nuclease is ideal for removal of nucleic acids from recombinant products, enabling compliance with FDA guidelines for nucleic acid contamination.

It was observed herein, that Benzonase® nuclease significantly reduced the DNA level in the VSV purification process and the final VSV purified bulk concentrate. However, the addition of Benzonase® nuclease prior to purification on the Mustang™ Q membrane adsorber resulted in the reduction of virus titer (data not shown). In contrast, Benzonase® nuclease treatment after the membrane chromatography purification step did not have the same effect (i.e., no titer reduction was observed).

However, because the complete VSV purification process described herein (e.g., see FIG. 1) removed greater than 99% of the cell culture contaminants, the DNA level in final VSV purified bulk concentrate was below the specification (e.g., WHO specification <10 ng/dose) without Benzonase® nuclease treatment. Thus, Benzonase® nuclease treatment does not have to be used in VSV purification process, which was a significant improvement compared with the traditional virus product/viral vaccine purification processes (which require Benzonase® nuclease treatment).

Mustang™ Q Binding Capacity. The binding capacity of the Mustang™ Q membrane adsorber was determined by VSV break-through using a small volume (0.35 ml volume) Mustang™ Q membrane adsorber (i.e., a Mustang™ Q coin). When loading and purifying conditioned cell culture fluid onto the Mustang™ Q coin, it was initially observed that VSV break-through could not be measured by UV absorbance because of the flow-through of UV absorbing impurities. Thus, in this example, the VSV flow-through fractions were collected and VSV detected by SDS-PAGE and VSV titer assay. The Mustang™ Q equilibrium buffer was 10 mM HEPES pH 7.5, 0.3 mM NaCl, and 2% sucrose.

Surprisingly, the conventional chromatographic 1% breakthrough was not reached (see Table 8 below) even after loading 400 ml of cell culture fluid onto the Mustang™ Q coin (the VSV culture fluid titer was $6.9\times10^6$/ml). However, as shown in Table 8, a higher VSV titer in the flow-through was observed when the Mustang™ Q coin was loaded with the 400 ml culture fluid sample. Additionally, as the loading volume reached to 400 ml, the differential pressure in the coin increased to 1.8 Bar. Thus, it was concluded from this experiment, that 350 ml of conditioned culture fluid per 0.35 ml of Mustang™ Q membrane adsorber was the filter loading capacity, which was equivalent to 500 ml cell culture/ml membrane adsorber. Alternatively, the Mustang™ Q binding capacity can also be described as $6.9\times10^9$ pfu/ml membrane. In three consistency runs, the actual loading capacity (in virus titer) was slightly higher than this binding capacity, which did not affect the process performance. Thus, this data indicated that the determined binding capacity was a conservative capacity number, and as such, could easily be used in the large-scale manufacturing production.

TABLE 8

MUSTANG ™ Q LOADING CAPACITY STUDY

| Loading Volume[1] (ml) | VSV Titer[2] in the Flow-Through (pfu/ml) |
|---|---|
| 0-200 (FT1) | ND* |
| 200-300 (FT2) | $6.80\times10^3$ |
| 300-350 (FT3) | $8.80\times10^3$ |
| 350-400 (FT4) | $1.30\times10^4$ |

Figure 5A:
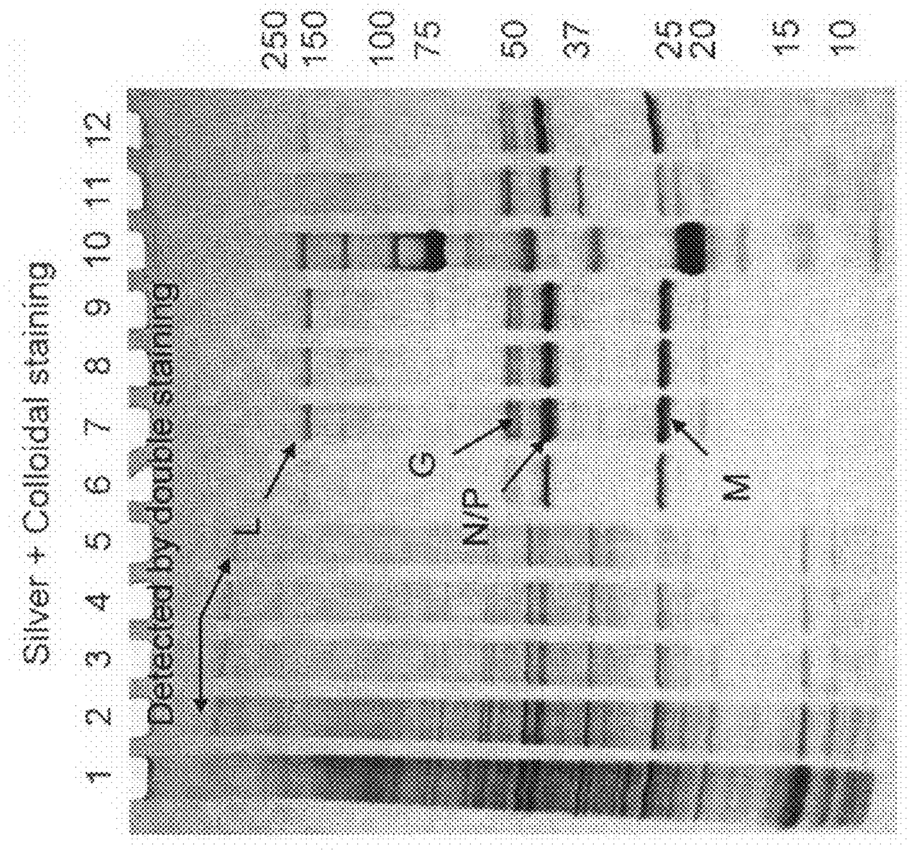
FIG. 5A is an SDS-PAGE (4-20% Tris-Glycine gel) comparison of VSV by silver+colloidal staining purified according to the process set forth in FIG. 1 versus VSV purified by sucrose gradient centrifugation (lane 11). Lanes 1-12 are (1) cell culture fluid, (2) post-centrifugation (1° clarification), (3) pre-0.2 μm filtration, (4) post-0.2 μm filtration (2° clarification), (5) flow-through and wash pool from the Mustang™ Q membrane adsorber, (6) VSV elution fractions from the Mustang™ Q membrane adsorber, (7) VSV retentate from the TFF UF/DF, (8) pre-0.2 μm (final) filtration, (9) post-0.2 μm (final) filtration (VSV purified bulk concentrate), (10) Bio-Rad® Precision Plus Protein™ standards, (11) VSV purified by sucrose gradient (only half the volume of lane 9 was added) and (12) VSV control (run #1, purified bulk concentrate).
Figure 5B:
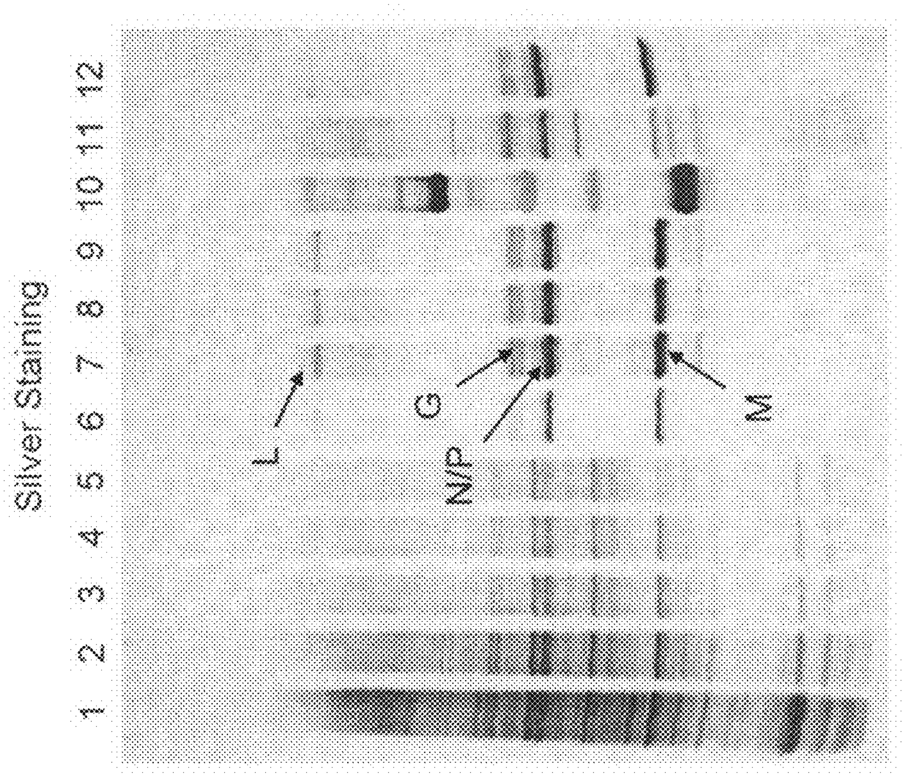
FIG. 5B is an SDS-PAGE (4-20% Tris-Glycine gel) comparison of VSV by Western Blot purified according to the process set forth in FIG. 1 versus VSV purified by sucrose gradient centrifugation (lane 11) as described in FIG. 5A.

ND* = not determined
Loading Volume[1] was based on the culture volume
VSV Titer[2]: the VSV feed titer was 6.9E+06/mL
Mustang ™ Q filter membrane volume was 0.35 ml
FT1-FT4 are Flow-Through 1-4, respectively Mustang™ Q Membrane Adsorber Conclusions. A high-quality VSV product with a high recovery was achieved with the Mustang™ Q membrane adsorber. Compared to "traditional" chromatographic processes, the Mustang™ Q purification process (in addition to being a straight forward and efficient process) has several advantages. For example, the process yields a VSV product of higher quality than purification by sucrose gradient ultracentrifugation (e.g., see FIGS. 5A and 5B). Furthermore, (a) the high binding capacity of the Mustang™ Q membrane adsorber means smaller process equipment and lower production cost, (b) the higher flow rate, relative to the other chromatographic resins tested, results in increased throughput and productivity and (c) the disposable Mustang™ Q membrane adsorber units eliminate the necessity of cleaning validation and lifetime validation.

The following summarizes the Mustang™ Q operating conditions developed and described above: (a) loading capacity=0.5 L cell culture per milliliter of Mustang™ Q membrane adsorber, (b) flow rate=20 capsule volumes (CV) per minute, (c) VSV binding pH=pH 7.5±0.1 pH unit, (d) VSV binding ionic strength=0.3±0.2 M salt; (e) VSV elution=step gradient in 15 CV and (f) VSV elution ionic strength=0.7 M salt.

Example 7

VSV Purification Process: Tangential Flow Filtration, Polishing, Buffer Exchange VSV concentration and buffer exchange were performed using a tangential flow filtration (TFF) ultrafiltration/diafiltration (UF/DF) system. The VSV elution pool from the Mustang™ Q membrane adsorber was in 10 mM HEPES buffer with a high (0.7 M NaCl) salt concentration and still had a trace amount of impurities. Thus, a UF/DF step was necessary to remove the residual impurities and produce a final VSV product in an appropriate product formulation buffer.

The elution pools from five Mustang™ Q experimental runs were combined and used in this experiment. A 16 $cm^2$ hollow TFF membrane cartridge with a molecular weight cut off of 750 kDa was utilized (GE Healthcare Bio-Sciences Corp., Piscataway, N.J.). The pooled solution was first concentrated to 10 ml. Five (5×) buffer exchanges in phosphate buffered saline (10 mM potassium phosphate buffer (PBS) at pH 7.1 and 138 mM NaCl) were performed.

The SDS-PAGE analysis for in-process samples indicated that the purified VSV was only present in the retentate and rinse, and VSV loss in the permeates was not detected by either silver staining or Western Blot analysis (data not shown). The SDS-PAGE data demonstrated that the VSV process recovery was acceptable and the impurities were removed gradually after each buffer exchange (data not shown). To completely remove the residual impurities, a total of five to six buffer exchanges were needed.

UF/DF Operating Condition Optimization. The effect of buffer composition on TFF UF/DF performance was investigated. The same Mustang™ Q elution pool was used as the feed for all the experiments (Table 9). The first three experiments were performed on a 16 $cm^2$ hollow fiber TFF membrane (GE Healthcare Bio-Sciences Corp.) while last run was finished with a 420 $cm^2$ TFF membrane (GE Healthcare Bio-Sciences Corp). For all experiments, product quality was similar (based on SDS-PAGE analysis and SE-HPLC).

TABLE 9

TFF BUFFER COMPOSITION EXPERIMENT

| Experimental Runs | Buffer | Recovery (%) |
|---|---|---|
| Experiment 1 | 10 mM HEPES, 0.15 M NaCl, pH 7.4, 4% Sucrose | 100.5 |
| Experiment 2 | 10 mM NaPi, pH 7.4, 4% Sucrose | 88.8 |
| Experiment 3 | 10 mM NaPi, 0.15 M NaCl, pH 7.4, 4% Sucrose | 80.6 |
| Experiment 4 | PBS, pH 7.2, 4% Sucrose | 80.0 |

Independent of the buffer used, there was no VSV product observed in diafiltration permeates (based on SDS-PAGE/silver staining; data not shown). However, total protein and DNA assays indicated that about 34-41% total protein loaded and 33-40% DNA loaded were removed in first three-diafiltration volumes. With regard to the buffer exchange, five diafiltration volumes (DV) were enough to reduce the permes, the following TFF UF/DF operating conditions were developed as follows:

ate conductivity to a satisfactory level.

Thu (a) TFF Membrane Cartridge: Hollow Fiber TFF Cartridge (750 kDa), (b) TFF Membrane capacity: 95 L cell culture/$m^2$, (c) Operating Pressure: p1=3-4 psig; p2=1-2 psig; TMP=1.5-2.5 psig, (d) Operating Temperature: room temperature, (e) Cross Flow Rate: 700 LMH, (f) Permeate Flux: >30 LMH, and (g) 5× Concentration and 6× Diafiltration into PBS+4% sucrose (10 mM potassium phosphate, 138 mM NaCl, pH 7.2);

wherein p1 is the inlet pressure, p2 is the outlet pressure, TMP is the transmembrane pressure and LMH is liters/$m^2$ hour.

Example 8

VSV Purification Process: Final Filtration

The last step in the VSV purification process was a final filtration of the TFF purified material described above. A 0.2 μm (0.45/0.2 μm) Sartorius Sartobran™ filter unit (Sartorius Corp.; Edgewood, N.Y.) at a flow rate of 100 ml per minute was used to remove possible bioburden with minimum loss of VSV product. The buffer was 10 mM potassium phosphate (pH 7.1-7.3), 138 mM NaCl and 7.5% sucrose.

Example 9

VSV Scale-Up Purification for $VSV_{IN}$ N4$CT_9$-gag1 Construct

Figure 6:
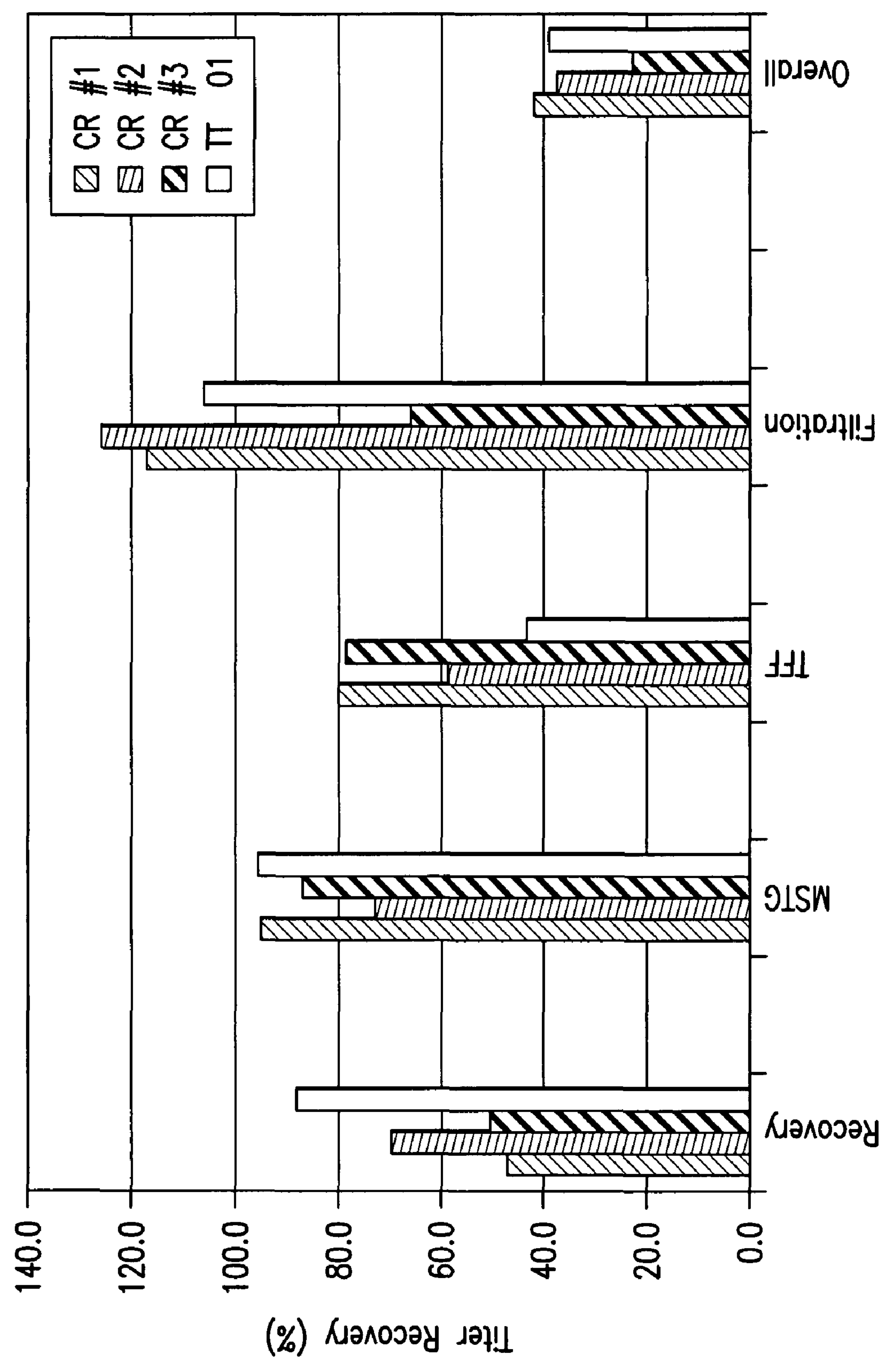
FIG. 6 is a bar graph showing the percent VSV titer recovery from the four scale-up runs (4.5 L in cell culture volume). CR #1 is experimental Run 1, CR #2 is experimental Run 2, CR #3 is experimental Run 3 and TT 01 is experimental Run 4.

Four 4.5 L scale-up runs (i.e., cell culture volume) were performed. The summaries of these scale-up runs are shown below in Table 10 and Table 11, and in FIG. 6. Assays including SDS-PAGE (data not shown), total protein (Table 11), virus titer (Table 10 and FIG. 6) and SE-HPLC (data not shown) were performed. Consistent process performance (i.e., VSV product quality) and impurity removal was achieved in each of the scale-up runs, using the process set forth in FIG. 1.

TABLE 10

SCALE-UP RUNS

| Run | Feed | | Purified Bulk Concentrate | |
|---|---|---|---|---|
| | Volume (ml) | Titer (pfu/ml) | Volume (ml) | Titer (pfu/ml) |
| 1 | 4192 | $5.60 \times 10^7$ | 475 | $2.40 \times 10^8$ |
| 2 | 4392 | $9.10 \times 10^7$ | 440 | $3.40 \times 10^8$ |
| 3 | 4425 | $5.20 \times 10^7$ | 475 | $1.10 \times 10^8$ |
| 4 | 4450 | $5.01 \times 10^7$ | 435 | $2.00 \times 10^8$ |

TABLE 11

PROTEIN IMPURITY REMOVAL IN VSV SCALE-UP RUNS

| Process Step | Total Protein Recovery (%) | | | |
|---|---|---|---|---|
| | Run 1 | Run 2 | Run 3 | Run 4 |
| Low Speed Centrifugation | ND | 91.0 | 73.2 | 91.5 |
| Pre-0.2 μm Filtration (Dilution) | 89.9 | 75.2 | 71.3 | 68.0 |
| Post-0.2 μm Filtration (Sartobran ™) | 100.6 | 97.3 | 102.6 | 98.1 |

TABLE 11-continued

PROTEIN IMPURITY REMOVAL IN VSV SCALE-UP RUNS

| Process Step | Total Protein Recovery (%) | | | |
|---|---|---|---|---|
| | Run 1 | Run 2 | Run 3 | Run 4 |
| Mustang ™ Q | 0.43 | 0.39 | 0.33 | 0.41 |
| UF/DF | 42.7 | 52.0 | 48.7 | 47.5 |
| Pre-0.2 μm Filtration | 95.7 | 106.8 | 104.5 | 99.4 |
| Post-0.2 μm Filtration (Sartobran ™) | 87.7 | 82.7 | 81.5 | 93.8 |
| Total Protein Removal (%) | ND | 99.9 | 99.9 | 99.9 |

ND = Not Determined

Analysis of the VSV Scale-Up Purification Process

The objective of developing the novel VSV purification process described herein (e.g., see FIG. 1) was to produce high purity VSV with a high recovery of the purified VSV product. The following analysis describes the VSV purification and stability based on four 4.5 L cell culture scale-up runs.

SDS-PAGE Analysis and Impurity Protein Removal. An important aspect of the purification process was depleting (or removing) the cell culture impurity proteins from the VSV product. As set forth above in Example 1, the $rVSV_{IN}$ construct exemplified herein was the $rVSV_{IN}$ N4$CT_9$-gag1 construct. The VSV product was monitored by detecting its major virus proteins, M (27 kDa), N/P (49 kDa), G (55 kDa) and L (250 kDa). Among the VSV proteins, M and N/P proteins were expressed at higher levels than the G ($CT_9$) and L proteins, wherein the L protein level was the lowest. Therefore the M and N/P proteins were observed with much more intensive bands in SDS-PAGE gel analysis relative to the G and L proteins. In all of the experiments, the same sample volumes were loaded into the gel (unless stated otherwise). Furthermore, instead of a single protein detection method such as silver stain or Coomassie® staining, silver/Coomassie® Blue double staining was utilized, thereby providing more sensitive protein detection.

The SDS-PAGE analysis for scale-up run number 4 (FIGS. 4A and 4B) revealed that the majority of host proteins were removed in the primary clarification step of low-speed centrifugation (FIGS. 4A, 4B, lanes 1 and 2) through the removal of cell debris. Based on BCA analysis, 91.5% of the total protein was removed, indicating that low-speed centrifugation was a significant impurity removal step.

Figure 4B:
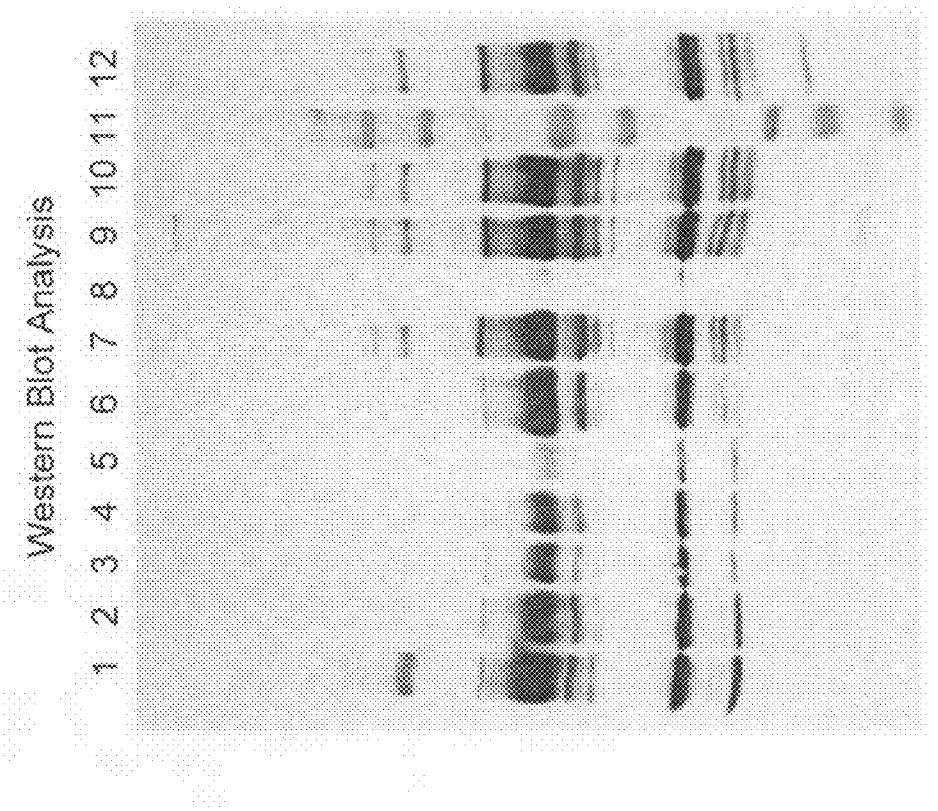
FIG. 4B is an SDS-PAGE analysis (4-20% Tris-Glycine gel) of VSV by Western blot according to the process described in FIG. 4A.
Figure 4A:
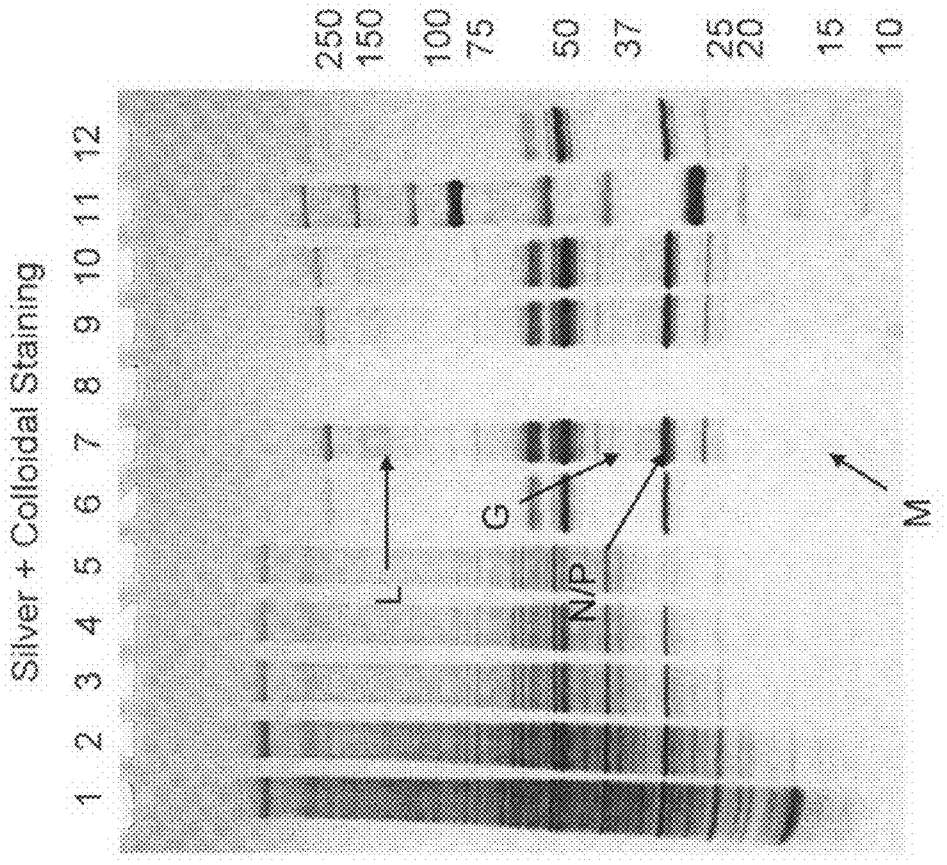
FIG. 4A is an SDS-PAGE analysis (4-20% Tris-Glycine gel) of VSV by silver+colloidal staining at each step of the purification process described in FIG. 1. Lanes 1-12 are (1) pre-centrifugation, (2) post-centrifugation (1° clarification), (3) pre-0.2 μm filtration, (4) post-0.2 μm filtration (2° clarification), (5) flow-through and wash pool from the Mustang™ Q membrane adsorber, (6) VSV elution fractions pool from the Mustang™ Q membrane adsorber, (7) VSV retentate from the TFF UF/DF, (8) concentrate and diafiltration pool, (9) pre-0.2 μm (final) filtration, (10) post-0.2 μm (final) filtration (VSV purified bulk concentrate), (11) Bio-Rad® Precision Plus Protein™ standards and (12) VSV control (run #3, purified bulk concentrate).

The supernatant from the centrifugation was diluted with 10 mM HEPES buffer (pH 7.5 after addition of 1× sucrose phosphate glutamate (SPG; 7.5% sucrose, 10 mM potassium phosphate, 5 mM glutamate)), 0.465 M NaCl and 2% sucrose (FIGS. 4A, 4B, lane 3), wherein a lighter staining band was observed due to dilution. The diluted solution was then pumped through a 0.2 μm filter to remove any remaining particulate contaminants (no impurity proteins were removed in this step; FIGS. 4A, 4B, lane 4). The VSV filtrate was collected as the feed for the Mustang™ Q step and loaded onto the membrane adsorber.

More than 99.5% of the remaining impurity proteins were removed on the Mustang™ Q membrane adsorber (Table 11). The removal of impurity proteins was observed by SDS-PAGE analysis (FIGS. 4A, 4B, lanes 4 and 5), wherein a high quality VSV product was eluted from the Mustang™ Q membrane (FIGS. 4A, 4B, lane 6).

The eluted VSV was concentrated and diafiltered into PBS buffer (+7.5% sucrose). More than 48% of the remaining protein impurities were removed in the UF/DF purification step (Table 11), wherein very intense VSV protein bands were detected (FIGS. 4A, 4B, lane 7). Only trace amounts of impurity proteins were observed in the UF/DF permeate pool (FIGS. 4A, 4B, lane 8). Before and after the final 0.2 μm filtration, there were no detectable changes with regard to VSV protein quality or impurity protein profile (FIGS. 4A, 4B, lanes 9 and 10).

The VSV purified bulk concentrate from the newly developed process also demonstrated higher purity and low residual level compared to purification via sucrose gradient centrifugation. For example, the staining bands of VSV proteins (M, N, P, G and L) from the newly developed process (FIGS. 5A, 5B, lane 9) were more intense than the staining bands of the VSV purified via sucrose gradient centrifugation (FIGS. 5A, 5B, lane 11) (with less intense impurity protein staining bands), indicating a higher quality VSV product was achieved by the novel purification process set forth in FIG. 1. In all four scale-up runs, similar product quality was achieved (data not shown) based on impurity protein profile and intensity of the VSV protein bands.

Size Exclusion-High Performance Liquid Chromatography (SE-HPLC) Analysis. A SE-HPLC analysis for VSV was developed (see, Example 1), which provides a simple and convenient method to separate VSV from impurity proteins and qualitatively analyze the VSV purification process. To protect the column, only clarified samples were injected into the column. The VSV flows out from the column as an elution peak with a retention time of 7.5 minutes (data not shown). The contaminant/impurity protein peaks (which have a longer column retention time) elute from the column after the VSV peak and therefore need to be eliminated/removed from the VSV product. The majority of impurities were removed in Mustang™ Q flow-through and wash, which confirms the results of SDS-PAGE analysis. In the UF/DF step, buffer related impurities were removed and no VSV was lost in any of the permeates (data not shown). Following the final 0.2 μm filtration, the VSV product eluted from the SE-HPLC column as a single major peak with retention time of 7.5 minutes, followed by two smaller peaks corresponding to buffer blank. (data not shown).

The Removal of Residual Host DNA. Cell culture (host cell) DNA is one of the major contaminants in purification processes using recombinant technology. The residual DNA level in VSV purified bulk concentrate should be below 10 ng/dose ($10^7$ pfu). The DNA removal profiles for the four scale-up runs are summarized below in Table 12, wherein consistent DNA removal was achieved in each purification step. Major DNA clearance was observed in the product recovery step (i.e., 1° clarification by low-speed centrifugation followed by 2° clarification by 0.2 μm filtration) and the Mustang™ Q membrane adsorber step. Greater than 80% of the residual DNA was removed in the Mustang™ Q step and more than 60% DNA clearance was achieved in UF/DF step. The overall percent DNA removal was 99.89±0.03% in all four scale-up runs. Furthermore, the residual DNA level was far below 10 ng/dose (Table 13).

TABLE 12

SUMMARY OF HOST DNA REMOVAL (%)

| Process Step | Run 1 | Run 2 | Run 3 | Run 4 | Average | Standard Deviation |
|---|---|---|---|---|---|---|
| Product Recovery[1] | 95.70 | 93.97 | 96.1 | 93.62 | 94.85 | 1.23 |
| Mustang ™ Q | 82.69 | 84.7 | 85.43 | 84.61 | 84.36 | 1.17 |
| TFF | 74.51 | 66.63 | 64.62 | 61.80 | 66.89 | 5.45 |
| Filtration | 44.81 | 64.23 | 55.34 | 57.73 | 55.53 | 8.07 |
| Overall | 99.90 | 99.89 | 99.91 | 99.84 | 99.89 | 0.03 |

Product Recovery[1] is the culture fluid clarification step of low-speed centrifugation followed by 0.2 μm filtration.

TABLE 13

SUMMARY OF DNA LEVEL IN VSV PURIFIED BULK CONCENTRATE

| | Residual DNA level (ng/$10^7$pfu-dose) |
|---|---|
| Run 1 | 1.46 |
| Run 2 | 0.97 |
| Run 3 | 3.00 |
| Run 4 | 1.93 |

The Removal of Gag Protein. The Gag protein concentration was determined by ELISA, which provided data to define residual Gag level in the VSV product. The profile of Gag protein in the purification process is summarized below in Table 14. The majority of the Gag protein was removed in the secondary clarification step (i.e., 0.2 μm filtration) and the Mustang™ Q membrane adsorber step. The residual Gag protein level ranged from 0.08 to 8.93 ng/dose ($10^7$ pfu) in the final purified bulk concentrate, as shown in Table 15.

TABLE 14

SUMMARY OF RESIDUAL GAG REMOVAL

| PROCESS | VOLUME (ML) | RESIDUAL GAG NG/ML | NG | OVERALL GAG REMOVAL |
|---|---|---|---|---|
| Unclarified culture | 4425 | 4.330 | 19160.3 | — |
| Post Centrifugation | 4373 | 3.530 | 15436.7 | 19.43% |
| Pre-0.2 μm filtration | 9272 | 0.750 | 6954.0 | 63.71% |
| Post-0.2 μm filtration | 9200 | 0.690 | 6348.0 | 66.87% |
| Flow-through + wash | 9800 | 0.660 | 6468.0 | — |
| Mustang ™ Q Elution | 1600 | 0.680 | 1088.0 | 94.32% |
| TFF Retentate | 450 | 4.100 | 1845.0 | 90.37% |
| Pre-0.2 μm filtration | 495 | 3.410 | 1688.0 | 91.19% |
| Purified Bulk Conc. | 475 | 0.930 | 441.8 | 97.69% |

TABLE 15

SUMMARY OF RESIDUAL GAG LEVEL IN VSV PURIFIED BULK CONCENTRATE

| | Gag removal (%) | Residual Gag level (ng/$10^7$ pfu-dose) |
|---|---|---|
| Run 1 | 80.0 | 8.93 |
| Run 2 | 87.1 | 6.76 |
| Run 3 | 97.7 | 0.08 |
| Run 4 | 87.1 | 8.50 |

Example 10

VSV Scale-Up Purification for $VSV_{IN}$ N4$CT_1$-gag1 Construct

The purification process development for the VSVinN4$CT_1$-gag1 construct was initially challenged with a low product titer in the cell culture fluid (<$10^6$ pfu/ml), which resulted a low product titer and high DNA contamination in final purified bulk concentrate. However, the purification process as described in Example 9 for $VSV_{IN}$N4$CT_9$-gag1 was successfully applied to this VSV construct and scaled-up to 10-L scale (in cell culture volume). A high-quality VSV product has been produced through this purification process.

In the purification process, the primary and secondary clarification steps were substantially similar to those described in Examples 3 and 4. The anion exchange membrane adsorption step using the Mustang™ Q adsorber was optimized as follows. Tangential flow filtration was conducted using Quixstand™ or Flexstand™ systems with hollow fiber membrane cartridges (GE Healthcare; Piscataway, N.J.). The GE polyethersulfone ultrafiltration membranes with molecular weight cut off (MWCO) of 750 kDa were also tested in this study. All membranes had a nominal filtration surface area of 420 $cm^2$ or 1200 $cm^2$. Membrane chromatography experiments were conducted using AKTA™ explorer and AKTAPilot™ systems (GE Healthcare; Piscataway, N.J.) with Pall Mustang™ Q membrane adsorbers (Pall Corporation; East Hills, N.Y.).

First Mustang™ Q Purification Trial for $VSV_{IN}$N4$CT_1$-gag1

The Mustang™ Q adsorption step was performed using the same buffers and operating conditions as described in $VSV_{IN}$N4$CT_9$-gag1 purification process. As a summary, the cell and debris were first removed through a centrifugation. After addition of 10× sucrose phosphate glutamate (SPG) in 1:9 ratio (v/v) and 2-fold dilution with 10 mM HEPES, 0.465 M NaCl, pH 7.5, 2% sucrose, the solution was pumped through a 0.2 μm filter. The filtrate was loaded into a pre-equilibrated Pall Mustang™ Q membrane adsorber (0.35-ml capsule volume), flow-through & wash (FT&W) pool was collected. VSV product was recovered in the elution pool using the same elution conditions described in $VSV_{IN}$N4$CT_9$-gag1 process. A high quality virus product was obtained (data not shown). However, one third of virus product was observed in the FT&W pool (Table 16), and the virus titer in the Mustang™ Q elution pool was very low due to the low virus production titer in the bioreactor (4.6×$10^5$ pfu/ml for $VSV_{IN}$N4$CT_1$-gag1 vs. >1.0×$10^7$ pfu/ml for $VSV_{IN}$N4$CT_9$-gag1).

TABLE 16

Process Analysis - Titer Recovery in the First Mustang ™ Q Step

| Process | Volume (ml) | Virus Titer (pfu/ml) | Virus Titer (pfu) | Recovery (%) |
|---|---|---|---|---|
| Feed | 250 | $9.90 \times 10^4$ | $2.48 \times 10^7$ | 100 |
| FT&W | 300 | $3.20 \times 10^4$ | $9.60 \times 10^6$ | 38.8 |
| Elution | 35 | $5.70 \times 10^5$ | $2.00 \times 10^7$ | 80.6 |
| Regeneration | 15 | $1.44 \times 10^5$ | $2.16 \times 10^6$ | 8.7 |

The binding conditions for this construct on Mustang™ Q adsorber were further optimized as follows. The experimental design is outlined in Table 17. In all experiments, the loading and elution pH from 6.5 to 7.5 was selected based on previous experiences from $VSV_{IN}$N4$CT_9$-gag1. The NaCl concentration in the loading buffer ranging from 0.28 to 0.32 M, while that in the elution buffer from 0.6 to 0.7 M were chosen in the experiments. The flow rate was 3.5-10.5 ml/min, which was equivalent to 10-30 capsule volume (CV)/min.

TABLE 17

Optimized Design for Mustang ™ Q Step

| Exp # | Loading pH | Loading NaCl (M) | Elution pH | Elution NaCl (M) | Flow rate (ml/min) |
|---|---|---|---|---|---|
| 1 | 7.0 | 0.30 | 7.0 | 0.6 | 7.0 |
| 2 | 6.5 | 0.32 | 6.5 | 0.7 | 3.5 |
| 3 | 7.5 | 0.32 | 6.5 | 0.5 | 3.5 |
| 4 | 7.5 | 0.32 | 7.5 | 0.7 | 10.5 |
| 5 | 6.5 | 0.28 | 6.5 | 0.5 | 10.5 |
| 6 | 7.5 | 0.28 | 6.5 | 0.7 | 10.5 |
| 7 | 7.5 | 0.28 | 7.5 | 0.5 | 3.5 |
| 8 | 7.0 | 0.30 | 7.0 | 0.6 | 7.0 |
| 9 | 6.5 | 0.28 | 7.5 | 0.7 | 3.5 |
| 10 | 6.5 | 0.32 | 7.5 | 0.5 | 10.5 |

Figure 7:
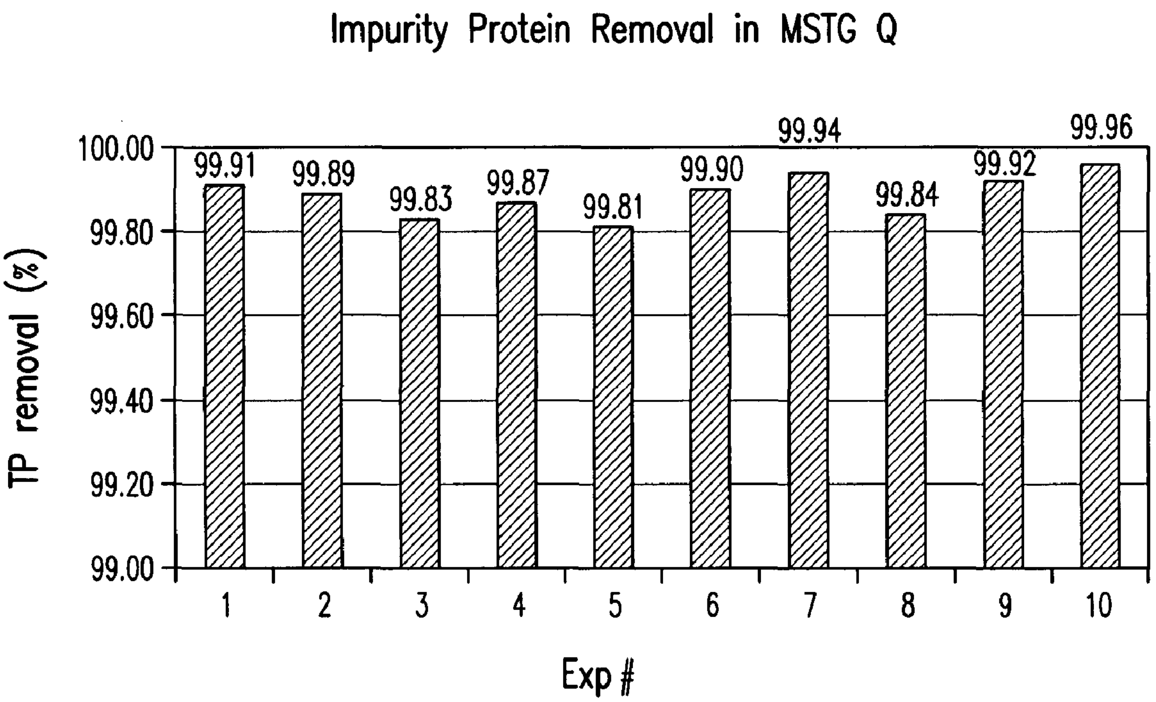
FIG. 7 is a bar graph showing the impurity protein removal in the Mustang™ Q purification step for the $VSV_{IN}N4CT_1$-gag1 construct.

A high-quality VSV product was observed in all Mustang™ Q elution pools based on SDS-PAGE analysis (not shown). Impurity protein removal results in this step are shown in FIG. 7. More than 99% of impurity proteins were removed in this single step, which was higher than that in $VSV_{IN}$N4$CT_9$-gag1 purification process. Process recovery and the results of residual host DNA assay in the elution pools are summarized in Table 18. The residual DNA level in elution pools was very low in all experiments, which indicates that the DNA clearance was not a problem in this process. However, titer recovery varied depending on the experimental conditions.

TABLE 18

The titer recovery and residual DNA level in Mustang ™ Q elution pools

| Exp # | Titer Recovery (%) | Residual DNA (ng/ml) |
|---|---|---|
| 1 | 78.1 | 1 |
| 2 | 32.2 | BD* |
| 3 | 23.9 | 1 |
| 4 | 35.7 | 1 |
| 5 | 39.1 | BD |
| 6 | 58.3 | BD |
| 7 | 52.2 | 3 |
| 8 | 87.5 | BD |
| 9 | 55.1 | BD |
| 10 | 23.7 | BD |

*BD indicates that DNA level is below the detection level

The process recovery was calculated from the virus titer determined by the plaque assay. When loading buffer pH was in the range of 6.6 to 7.5, and NaCl concentration was from 0.28 to 0.30 M, an acceptable process recovery was achieved as shown in a contour plot (data not shown). The optimal loading buffer condition was 0.29 M NaCl in 10 mM HEPES, 2% sucrose, pH 7.0. Considering that no pH adjustment was preferred in the feed conditioning, pH 7.5 was considered acceptable for the Mustang™ Q equilibration buffer pH. At the same time, 0.60-0.70 M NaCl and pH 6.75-7.25 were determined as the Mustang™ elution buffer conditions. The optimal elution buffer condition was 10 mM HEPES, 0.65 M NaCl, 2% sucrose, pH 7.0. The Mustang™ Q buffer conditions are summarized in Table 19. With these developed conditions, the DNA contaminants in elution pools were reduced to an acceptable level (data not shown).

TABLE 19

| Mustang ™ Q buffer conditions | | |
|---|---|---|
| Process | pH | NaCl Concentration (M) |
| Equilibration | 6.6-7.5 | 0.28-0.30 |
| Elution | 6.75-7.25 | 0.60-0.70 |

Further experiments were consistent with these results and demonstrated that in certain embodiments 0.28M to 0.30 M NaCl and a pH 7.2-7.5 were the preferred binding buffer conditions to insure a high product recovery, and an acceptable reduction in DNA contaminants in elution pools.

Example 11

VSV Scale-Up Purification for $VSV_{IN}N4CT_1$-gag1 Construct

Three confirmation runs in small scale were completed with the same feed materials using the above developed Mustang™ Q conditions. The equilibration buffer was 10 mM HEPES, 0.29 M NaCl, pH 7.5, 2% sucrose; while the elution buffer was 10 mM HEPES, 0.65 M NaCl, pH 7.0, 2% sucrose. The same operating conditions were maintained for all runs: same flow rate, same loading volume and same elution volume. The experimental results are summarized in Table 20. A very consistent process performance was achieved based on the product recovery calculated from titer assay results.

TABLE 20

| Mustang ™ Q confirmation runs | |
|---|---|
| Experimental runs | Recovery (%) |
| A | 73.0 |
| B | 81.4 |
| C | 70.8 |

$VSV_{IN}N4CT_1$-gag1 Purification Process Scale-Up, Consistency Runs and Tech Transfer The cell culture fluid containing $VSV_{IN}N4CT_1$-gag1 after removal of microcarriers was used as the starting materials for the whole purification process. The process comprised clarifying the cell culture fluid by low-speed centrifugation and recovering the VSV in the supernatant; filtering the supernatant through a 0.45/0.2 μm filter and recovering the VSV in the filtered solution; loading the VSV filtered solution onto an anion exchange membrane adsorber, recovering the VSV product in the elution pools; purifying the recovered VSV by tangential flow filtration (TFF) using a 750 kDa molecular weight cutoff membrane and recovering the VSV in the retentate, and finally filtering the VSV retentate through a 0.2 μm filter and recovering the VSV in the filtered solution. Three 6-L scale-up/consistency runs (CR) and one 10-L run (TTR) were completed successfully. The experimental conditions are summarized in Table 21.

TABLE 21

| Process conditions of VSVinN4CT1-gag1 scale-up/consistency runs | |
|---|---|
| Process | Process Conditions |
| Product recovery by centrifugation | Batch centrifuge 6238 × g, 30 min, 20-24° C. |
| Product recovery by filtration | Sartorius Sartobran ™ 300 (for 6-L scale), 500 (for 10-L scale); Flow rate: 200 ml/min (for 6-L scale) and 300 ml/min (for 10-L scale) |
| Mustang ™ Q chromatography | Pall Mustang ™ Q 10 ml capsule, Flow rate: 200 ml/min; Pall Mustang ™ Q 60 ml capsule, Flow rate: 600 ml/min |
| Ultrafiltration/diafiltration | GE Healthcare, MWCO: 750 kDa; Five buffer exchanges; CR: 420 $cm^2$, CFR: 500-550 ml/min, TMP = 1.0-2.0 psi; TTR: 1200 $cm^2$, CFR: 1800 ml/min, TMP = 2.0 psi |
| Final filtration | Sartorius Sartobran ™ 150; 100 ml/min |

The experimental results are summarized in Tables 22 and 23. A typical SDS-PAGE analysis for the process was performed (data not shown). The variation of step recovery among different runs was due to the variation of the potency assay (plaque assay). Overall process yield was consistent for the performed runs. A consistent removal of protein and DNA impurities was observed. For all runs, a high-quality virus product was produced.

TABLE 22

| Summary of $VSV_{IN}N4CT_1$-gag1 consistency runs | | | | |
|---|---|---|---|---|
| | Scale-up | CR#1 | CR#2 | TTR #1 |
| Batch # | VSV060405 | VSV060816 | VSV060831 | LP#1 |
| Cell culture harvest: Volume (ml) | 6612 | 5696 | 5692 | 8000 |
| Cell culture harvest: Titer (pfu/ml) | $5.55 \times 10^5$ | $2.15 \times 10^5$ | $1.69 \times 10^6$ | $8.14 \times 10^5$ |
| Purified bulk concentrate Vol (ml) | 280 | 530 | 280 | 850 |
| Purified bulk concentrate Titer (pfu/ml) | $1.45 \times 10^6$ | $2.08 \times 10^5$ | $3.00 \times 10^6$ | $7.81 \times 10^5$ |
| Process Yield (%) | 11.7 | 9.1 | 8.7 | 10.2 |
| Residual DNA (ng/ml) | 32 | 12 | 13 | 6 |
| Impurity protein removal (%) | N/D | 99.97 | 99.98 | 99.92 |

N/D: not determined

TABLE 23

| Process analysis based on the product recovery | | | | | | |
|---|---|---|---|---|---|---|
| Process step | CR#1 | CR#2 | Scale-up | Average[1] | STDEV[2] | TTR # 1 |
| Harvest | 100.0 | 100.0 | 100.0 | | | 100 |
| Centrifugation | 56.6 | 70.0 | 79.3 | 68.6 | 11.4 | N/D |
| Pre SB dilution | 137.0 | 112.5 | N/D | 124.8 | 17.3 | 23.7 |
| Sartobran filtration | 96.5 | 71.8 | 98.1 | 88.8 | 14.7 | 257.2 |
| Overnight storage | 89.8 | 41.9 | N/D | 65.9 | 33.9 | 48.6 |
| Mustang Q | 43.4 | 100.1 | 32.9 | 58.8 | 36.2 | 93.0 |
| UF/DF | 58.4 | 99.2 | 110.0 | 89.2 | 27.2 | 26.4 |
| 0.2 mm filtration | 53.6 | 37.0 | 39.4 | 43.3 | 9.0 | 139.7 |
| Overall yield | 9.1 | 8.7 | 11.7 | 9.8 | 1.6 | 10.2 |

[1,2]Average and STDEV of CR #1-3;
N/D: not determined.

The purification process for $VSV_{IN}N4CT_1$-gag1 was successful in producing a high quality product. The purification conditions were scaled up to 10-L scale (in cell culture volume) with a consistent process performance. The overall process yield based on the VSV titer from the plaque assay was lower than that achieved from $VSV_{IN}N4CT_9$-gag1 and $VSV_{NJ}N4CT_1$-gag1. The major titer loss was observed in final 0.2 μm filtration and also possibly in Mustang™ Q step. The non-specific binding might explain the loss especially when the study was challenged by the low-titer starting materials. The lower the titer, a larger portion of the virus would be lost in the filters. Increasing the VSV titer at the cell culture was a good resolution. Different buffer components, excipents and operating conditions for use in reducing the virus titer loss in the purification process and selection of a virus-product friendly buffer system are modifications to this purification system that are believed to be within the skill of the art without resort to undue experimentation.

Example 12

VSV Scale-Up Purification for $VSV_{NJ}N4CT_1$-gag1 Construct

The purification process as described in Example 9 for $VSV_{IN}N4CT_9$-gag1 was successfully applied to this VSV construct and scaled-up to 10-L scale (in cell culture volume). A high-quality VSV product has been produced through this purification process.

In the purification process, the primary and secondary clarification steps were substantially similar to those described in Examples 3 and 4. The anion exchange membrane adsorption step using the Mustang™ Q adsorber was optimized as follows. Tangential flow filtration was conducted using Quixstand™ or Flexstand™ systems with hollow fiber membrane cartridges (GE Healthcare; Piscataway, N.J.). The GE polyethersulfone ultrafiltration membranes with molecular weight cut off (MWCO) of 750 kDa were tested in this study. All membranes had a nominal filtration surface area of 420 $cm^2$ or 1200 $cm^2$. Membrane chromatography experiments were conducted using AKTA™ explorer and AKTAPilot™ systems (GE Healthcare; Piscataway, N.J.) with Pall Mustang™ Q membrane adsorbers (Pall Corporation; East Hills, N.Y.).

The first Mustang™ Q purification trial for $VSV_{NJ}N4CT_1$-gag1 produced a high quality product based on SDS-PAGE analysis, utilizing the same operating conditions described in $VSV_{IN}N4CT_9$-gag1 purification process. However, a high residual DNA level was detected in the product elution pool. Using membrane chromatography, the Mustang™ Q binding and elution conditions were developed to achieve a high purification fold and a high-quality VSV product. A high process performance consistency was demonstrated in later experiments including small-scale runs, and scale-up/consistency runs, using the following operating conditions. The purification process was also successfully transferred to contract manufacturing organization (CMO) for clinical trial materials production.

First Mustang™ Q Purification for $VSV_{NJ}N4CT_1$-gag1

The Mustang™ Q step was performed using cell culture fluid and the same buffers and operating conditions as described in $VSV_{IN}N4CT_9$-gag1 purification process. As a summary, the cell and debris were removed through centrifugation. After conditioned by addition of 1× sucrose phosphate glutamate (SPG) and 2-fold dilution with 10 mM HEPES, 0.465 M NaCl, pH 7.5, 2% sucrose, the supernatant was pumped through a 0.2 μm filter. The filtrate was loaded to a pre-equilibrated Mustang™ Q membrane adsorber, flow-through and wash pool was collected. VSV product was obtained by using the elution buffer and operating conditions as described in $VSV_{IN}N4CT_9$-gag1 purification process. A pool from the regeneration using 10 mM HEPES, 1.0 M NaCl, pH 7.5, 2% sucrose was also collected. Finally, Mustang™ Q was cleaned with 1.0 M NaOH solution. A high VSV binding capacity was observed in the experiment. However, very little product was recovered in the elution pool (data not shown). The virus product was dominantly detected in the regeneration pool, and, more than half of virus product was not recovered (see, Table 24) at all. A high level of DNA contaminants were detected in both elution and regeneration pools. The binding and elution conditions for Mustang™ Q were further optimized for this new construct to increase the product recovery and reduce the residual DNA level at the same time.

TABLE 24

| Mustang ™ Q process analysis - titer recovery and DNA removal | | | | |
|---|---|---|---|---|
| | PROCESS: | | | |
| | Feed | FT&W | Elution | Regeneration |
| Volume (ml) | 312 | 330 | 35 | 15 |
| Virus Titer (pfu/ml) | $6.71 \times 10^5$ | BD | $5.94 \times 10^5$ | $5.00 \times 10^6$ |
| Virus Titer (pfu) | $2.09 \times 10^8$ | BD | $2.08 \times 10^7$ | $7.50 \times 10^7$ |
| Virus Recovery (%) | 100.0 | 0.0 | 9.9 | 35.8 |
| DNA (ng/ml) | 123 | 16 | 84 | 782 |
| DNA (ng) | 38376 | 5280 | 2940 | 11730 |
| DNA Recovery (%) | 100.0 | 13.76 | 7.66 | 30.57 |
| DNA (ng/dose*) | 1833.1 | n/a | 1414.1 | 1564.0 |

*1 dose = $1.0 \times 10^7$ pfu;
BD: below detection limit

As described previously, $VSV_{IN}N4CT_9$-gag1 purification was challenged by residual DNA clearance from the final product. Merck KGaA™ TMAE and Pall Mustang™ Q were used for further condition optimization.

VSV Purification Development Using TMAE™ Resin

The VSV binding buffer condition screening on TMAE™ resin was performed using a full factorial experimental design as shown in Table 25. The feed was cell culture supernatant adjusted to different loading buffer conditions. VSV in the flow-through was monitored using western blot analysis.

TABLE 25

| Full factorial design for TMAE ™ binding conditions | | |
|---|---|---|
| Factors | pH | NaCl concentration in equilibration buffer (mM) |
| Level | 6.5, 7.0, 7.5 | 0, 50, 100, 150, 200, 250, 300, 400 |

Figure 8A:
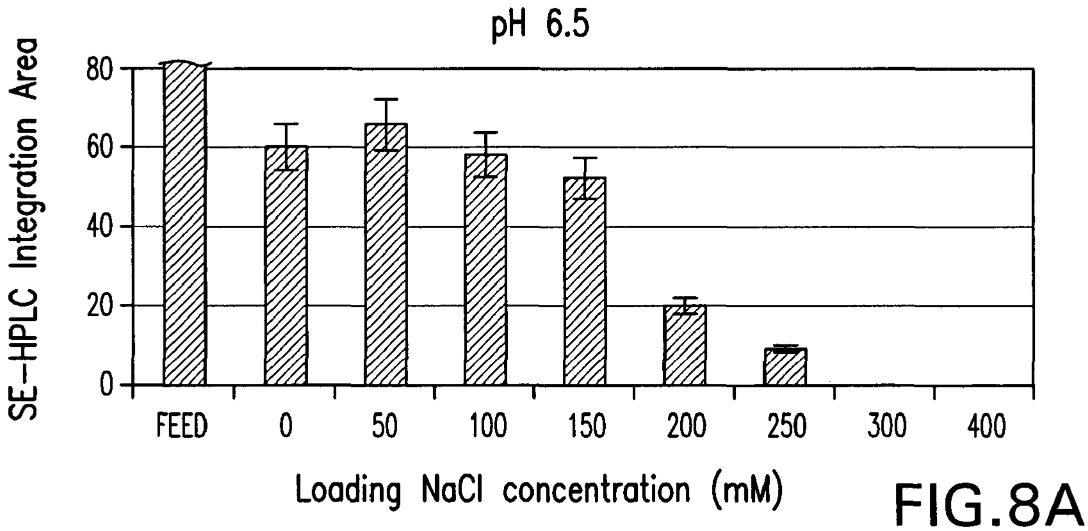
FIG. 8A is a bar graph showing the $VSV_{NJ}N4CT_1$-gag1 recovery in TMAE condition screening at pH 6.5.
Figure 8B:
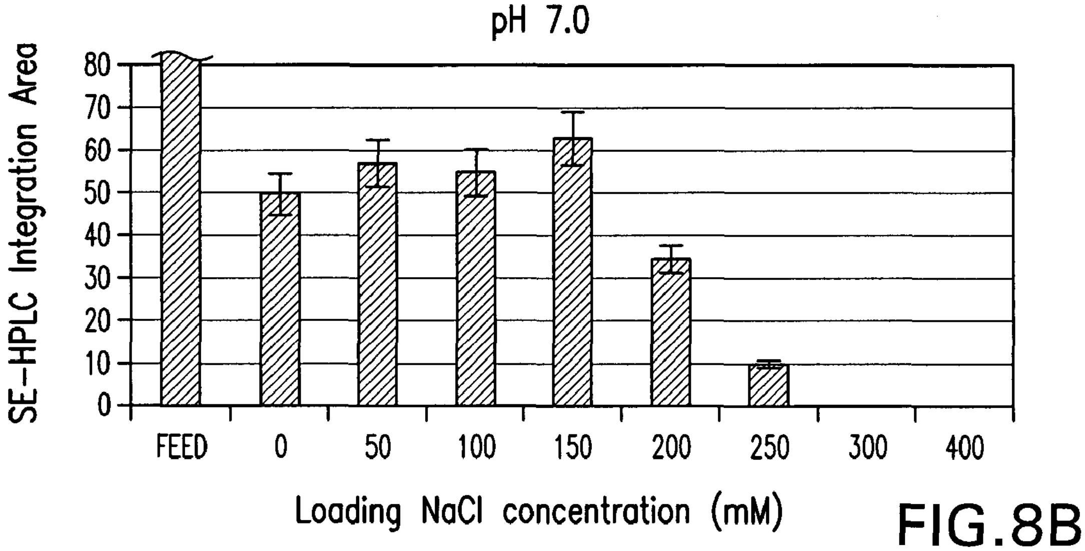
FIG. 8B is a bar graph showing the $VSV_{NJ}N4CT_1$-gag1 recovery in TMAE condition screening at pH 7.0.
Figure 8C:
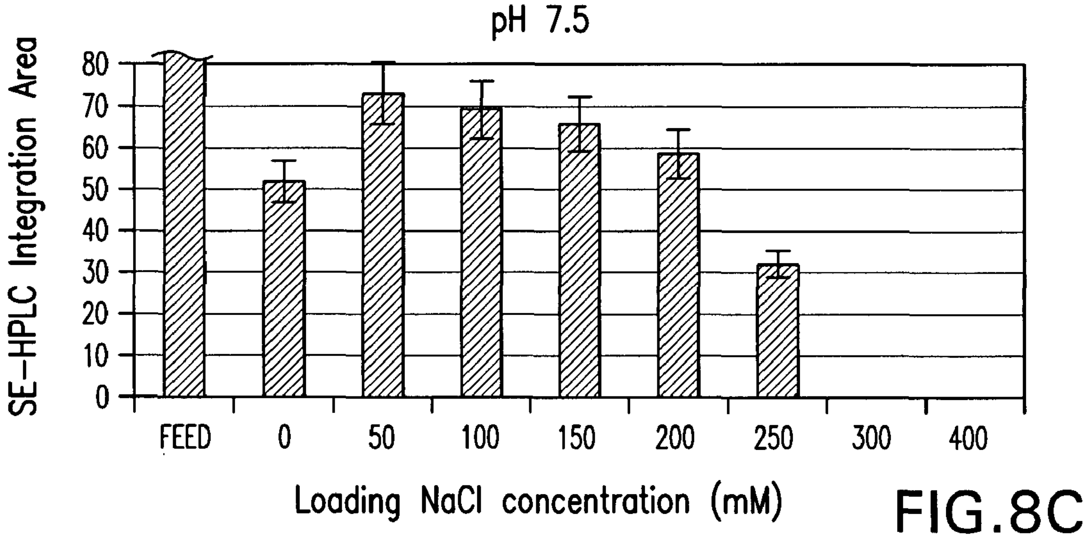
FIG. 8C is a bar graph showing the $VSV_{NJ}N4CT_1$-gag1 recovery in TMAE condition screening at pH 7.5.

As indicated by Western blot analysis (not shown), when NaCl concentration in equilibration buffer reached 200 mM, a significant amount of VSV was observed in the flow-through pools. To obtain a reasonable VSV binding capacity on TMAE, NaCl concentration in the equilibration buffer should be below 200 mM. The binding behavior of VSV was not dramatically affected within the tested pH conditions. However, the analysis of VSV recovery in the elution pool (estimated by SE-HPLC peak integration area of TMAE elution pool (FIGS. 8A, 8B and 8C) indicated that at the same binding NaCl concentration, a higher capacity was achieved at higher pH condition (pH 7.5 vs. pH 7.0 and 6.5).

VSV Purification Trial Using TMAE Column

The cell and cell debris were removed from the cell culture fluid containing $VSV_{IN}N4CT_9$-gag1 through a centrifugation at 5000 rpm for 30 minutes at 20-24° C. The supernatant was pumped through a 0.45/0.2 μm filter after mixed with 10×SPG stock solution in a ratio of 9 to 1. The filtrate was used as the feed to TMAE column (2 ml) at a flow rate of 4 ml/min. The column was pre-equilibrated with 10 mM HEPES, 0.145 M NaCl, 2% sucrose, pH 7.4. After chasing the column with 10 column volume (CV) of equilibration buffer, the bound materials were eluted from the column through a linear gradient to 10 mM HEPES, 1.5 M NaCl, 2% sucrose, pH 7.5 in 30 CV. Different elution pools were collected.

TABLE 26

| VSV elution from a TMAE column | | |
|---|---|---|
| Samples | Description | Volume (ml) |
| Feed | Post 0.2 μm filter | 130 |
| FT&W | Flow-through and wash | 150 |
| F1 | A3-10 | 16 |
| F2 | A11-B12 | 6 |
| F3 | B11-B1 | 22 |
| F4 | C12-D11 (0.5 M NaOH) | 6 |

SDS-PAGE gel electrophoresis (not shown) permitted observation of two main peaks in the elution profile. The first peak F1 had low UV254/280 ratio, indicating higher protein/virus contents. The second peak F2 had high UV254/280 ratio, suggesting a higher nucleic acid contents. PicoGreen® assay confirmed that DNA level in fraction pool F1 was extremely low (data not shown). Therefore, this column was used for DNA removal. The titer recovery in this peak was 81.4% by plaque assay. However, a high level of protein impurities was noted.

VSV Purification Using Mustang™ Q Membrane Adsorber

The VSV binding condition screening on Mustang™ Q membrane adsorber was performed, using a full factorial experimental design as shown in Table 27. The feed was cell culture supernatant adjusted to different loading buffer conditions. Different Mustang™ Q elution pools were analyzed using SDS-PAGE analysis (not shown)

TABLE 27

| Full factorial design for Mustang ™ Q binding condition screening | | |
|---|---|---|
| Factors | pH | NaCl concentration in equilibration buffer (mM) |
| Level | 6.5, 7.0, 7.5 | 0.15, 0.20, 0.22, 0.24, 0.26, 0.28 |

The SDS-PAGE analysis of the VSV binding condition screening on Mustang™ Q adsorber showed elution pools at different binding NaCl concentrations respectively: 0.15, 0.20, 0.22, 0.24, 0.26, 0.28 M. When NaCl concentration in equilibration buffer reached 0.26 M, the high-molecular-weight protein impurities were removed from the elution pools at all tested pH conditions.

Elution Condition Screening

The cell culture supernatant containing $VSV_{IN}N4CT_9$-gag1 was diluted two-fold with a HEPES stock solution (10 mM HEPES, 0.415 M NaCl, 2% sucrose, pH 7.25) to reach a final NaCl concentration of 0.28 M. The prepared solution was used as the feed of experiment. The experimental design for this study is summarized in Table 28. After binding to Mustang™ Q MA, the VSV was eluted with elution buffers at different NaCl concentrations.

TABLE 28

| Full factorial design for Mustang ™ Q elution condition screening study | | |
|---|---|---|
| Factors | pH | NaCl concentration in elution buffer (M) |
| Level | 6.5, 7.0, 7.5 | 0.55, 0.60, 0.65, 0.70 and 0.75 |

A contour plot analysis of process recovery (not shown) indicates that in order to get a reasonable process recovery (>55%), the elution buffer conditions should be maintained as: pH=6.5-6.9 and NaCl concentration=0.55-0.70 M. With these conditions, a high-quality VSV product has been produced as shown in SDS-PAGE analysis for Mustang™ Q elution pools (not shown).

Mustang™ Q Condition Optimization Using DOE Approaches

Further optimization in Mustang™ Q step resulted in better VSV binding and elution conditions to achieve a high level of DNA clearance and high process yield. The experimental design is shown in Table 29. The loading and elution pH from 6.5 to 7.0 was selected based on initial screening studies and previous experiences in $VSV_{IN}N4CT_9$-gag1. Different NaCl concentrations in loading and elution buffers were also chosen from the results of initial screening studies. The flow rate in all experiments was maintained at 7.0 ml/min, which was 20 capsule volume (CV)/min.

TABLE 29

| VSV purification on Mustang ™ Q adsorber | | | | |
|---|---|---|---|---|
| Exp # | Binding NaCl (M) | Binding pH | Elution NaCl (M) | Elution pH |
| 1 | 0.26 | 6.5 | 0.550 | 6.50 |
| 2 | 0.26 | 6.5 | 0.700 | 6.75 |
| 3 | 0.26 | 7.0 | 0.625 | 7.00 |
| 4 | 0.26 | 7.5 | 0.550 | 6.75 |
| 5 | 0.26 | 7.5 | 0.700 | 6.50 |
| 6 | 0.28 | 6.5 | 0.550 | 7.00 |
| 7 | 0.28 | 6.5 | 0.625 | 6.50 |
| 8 | 0.28 | 7.0 | 0.550 | 6.50 |
| 9 | 0.28 | 7.0 | 0.625 | 6.75 |
| 10 | 0.28 | 7.0 | 0.625 | 6.75 |
| 11 | 0.28 | 7.0 | 0.625 | 6.75 |

TABLE 29-continued

VSV purification on Mustang ™ Q adsorber

| Exp # | Binding NaCl (M) | Binding pH | Elution NaCl (M) | Elution pH |
|---|---|---|---|---|
| 12 | 0.28 | 7.0 | 0.625 | 6.75 |
| 13 | 0.28 | 7.5 | 0.700 | 7.00 |
| 14 | 0.30 | 6.5 | 0.550 | 6.50 |
| 15 | 0.30 | 6.5 | 0.700 | 7.00 |
| 16 | 0.30 | 7.0 | 0.625 | 6.75 |
| 17 | 0.30 | 7.0 | 0.700 | 6.50 |
| 18 | 0.30 | 7.5 | 0.550 | 7.00 |
| 19 | 0.30 | 7.5 | 0.625 | 6.50 |

Experimental Results

The process yield was calculated based on the VSV product titer determined by the plaque assay. The results are summarized on a prediction profile (not shown). To maximize the process yield, the following buffer conditions in Mustang™ Q adsorption were identified:

NaCl concentration in loading buffer: 0.26-0.30 M

Loading buffer pH: 7.0-7.5

NaCl concentration in elution buffer: 0.55-0.65

Elution buffer pH: 6.5-7.0

The residual DNA levels in Mustang™ Q elution pools at different binding conditions were reported in contour plots (not shown). The Mustang™ Q buffer conditions were further refined based on the DNA clearance results:

NaCl concentration in loading buffer: 0.27-0.29 M

Loading buffer pH: 7.0-7.5

NaCl concentration in elution buffer: 0.55-0.65

Elution buffer pH: 6.5-7.0

The VSV product purity in Mustang™ Q elution pools was estimated by densitometry of SDS-PAGE (not shown). The product purity at different binding buffer conditions and at different elution buffer conditions was analyzed. Considering the variation of densitometry analysis, there was no significant difference in VSV product purity for all cases. A high-quality VSV product was produced in all experiments.

Mustang™ Q Operating Ranges

The binding and elution buffer conditions of Mustang™ Q membrane chromatography were defined by performing the experiments with more operating points within and outside the developed conditions as shown in Table 30. The equilibration/elution buffer was 10 mM HEPES, 2% sucrose with various amount of NaCl and different pH conditions. The same operating conditions were maintained in all the runs: same flow rate, same loading volume and same elution volume. A consistent process performance was observed as shown in Table 30: a high-quality VSV product was produced based on SDS-PAGE analysis; an acceptable level of residual DNA clearance was achieved in all Mustang™ Q elution pools; a similar process yield was obtained as well.

TABLE 30

Mustang ™ Q operating range experiment

| Loading pH | Loading NaCl (M) | Elution pH | Elution NaCl (M) | Yield (%, titer) | Purity (%, SDS/PAGE) | DAN (ng/ml) |
|---|---|---|---|---|---|---|
| 7.5 | 0.30 | 6.75 | 0.60 | 52.0 | 72.0 | 34 |
| 7.0 | 0.30 | 6.75 | 0.60 | 85.7 | 80.0 | 33 |
| 7.5 | 0.26 | 6.75 | 0.60 | 49.1 | 76.1 | 34 |
| 7.0 | 0.26 | 6.75 | 0.60 | 68.0 | 73.0 | 39 |
| 7.5 | 0.28 | 7.00 | 0.65 | 85.7 | 79.6 | 21 |
| 7.5 | 0.28 | 6.50 | 0.65 | 70.9 | 82.3 | 18 |
| 7.5 | 0.28 | 6.50 | 0.55 | 49.5 | 82.8 | 15 |

TABLE 30-continued

Mustang ™ Q operating range experiment

| Loading pH | Loading NaCl (M) | Elution pH | Elution NaCl (M) | Yield (%, titer) | Purity (%, SDS/PAGE) | DAN (ng/ml) |
|---|---|---|---|---|---|---|
| 7.5 | 0.28 | 7.00 | 0.55 | 59.9 | 83.3 | 21 |
| 7.5 | 0.28 | 6.75 | 0.60 | 52.6 | ND* | 17 |
| 7.5 | 0.28 | 6.75 | 0.60 | 107.2 | ND* | 30 |

N/D: not determined $VSV_{IN}N4CT_9$-gag1 Consistency Runs

The whole purification process was performed using cell culture fluid containing $VSV_{IN}N4CT_9$-gag1. The process comprises: clarifying the cell culture fluid by low-speed centrifugation and recovering the VSV in the supernatant; filtering the supernatant through a 0.45/0.2 μm filter and recovering the VSV in the filtered solution; loading the VSV filtrate onto an anion exchange membrane adsorber, eluting the VSV from the anion exchange membrane adsorber and recovering the VSV product; purifying the recovered VSV by tangential flow filtration (TFF) using 750 kDa molecular weight cutoff hollow fiber membrane and recovering the VSV in the retentate, and filtering the VSV retentate through a 0.2 μm filter and recovering the VSV in the filtered solution. One 10-L and two 6-L runs were completed at Wyeth as the "consistency runs" and two 10-L runs were accomplished at Henogen as the tech transfer runs. The experimental conditions are summarized in Table 31.

TABLE 31

Process conditions for $VSV_{IN}N4CT_9$-gag1 runs

| Process | Process Conditions |
|---|---|
| Product recovery by centrifugation | Batch centrifuge: 6236 × g, 30 min, 20-24° C. |
| Product recovery by filtration | Sartorius Sartobran ™ 300 for 6-L scale, 500 for 10-L scale; Flow rate: 200 ml/min for 6-L scale and 300 ml/min for 10-L scale |
| Mustang Q chromatography | Pall Mustang ™ Q 10 ml capsule, Flow rate: 200 ml/min; Pall Mustang ™ Q 60 ml capsule, Flow rate: 600 ml/min |
| TFF Ultrafiltration/ Diafiltration | GE Healthcare, MWCO: 750 kDa, Five buffer exchanges; CR: 420 $cm^2$, CFR: 500-550 ml/min, TMP = 1.0-2.0 psi; TTR: 1200 $cm^2$, CFR: 1800 ml/min, TMP = 2.0 psi |
| Final filtration | Sartorius Sartobran ™ 150; Flow rate: 100 ml/min |

A 10-ml Mustan™ Q capsule was used in three consistency runs (CRs) and one tech transfer run (TTR). 60-ml Mustang™ Q capsule was only used in one TTR. The flow rate was 200 ml/min for 10-ml capsule and 600 ml/min for 60-ml capsule. 420 $cm^2$ TFF membrane was used in the consistency runs while 1200 $cm^2$ was used in TTRs. The cross flow rate was adjusted linearly according to the membrane area.

The experimental results are summarized in Tables 32 and 33. Overall process yield was consistent for all performed runs. The variation of step recovery among different runs due to the variation of the potency assay (Table 33). A consistent removal of protein and DNA impurities were observed in all the runs (Table 32). A typical SDS-PAGE analysis for the process accompanied this evaluation (not shown). A high-quality virus product was produced through this purification process.

TABLE 32

Summary of $VSV_{NJ}N4CT_1$-gag1 consistency runs

| | CR#1 | CR#2 | CR#3 | TTR#1 | TTR#2 |
|---|---|---|---|---|---|
| Batch # | VSV060629 | VSV060712 | VSV060728 | Henogen #1 | Henogen #2 |
| Cell culture harvest: Volume (ml) | 8927 | 5704 | 5607 | 8072 | 7980 |
| Cell culture harvest: Titer (pfu/ml) | $1.28 \times 10^7$ | $2.81 \times 10$ | $2.56 \times 10^7$ | $1.27 \times 10^7$ | $8.14 \times 10^6$ |
| Purified bulk concentrate Vol (ml) | 800 | 670 | 600 | 855 | 550 |
| Purified bulk concentrate Titer (pfu/ml) | $8.22 \times 10^7$ | $1.45 \times 10^8$ | $1.16 \times 10^8$ | $2.86 \times 10^7$ | $5.36 \times 10^7$ |
| Process Yield (%) | 57.7 | 60.8 | 55.8 | 23.9 | 45.4 |
| Residual DNA (ng/ml) | 18 | 22 | 11 | 51 | 21 |
| Impurity protein removal (%) | 99.83 | 99.84 | 99.89 | 99.72 | NA |

NA: not available

TABLE 33

Process analysis based on the product recovery

| Process step | CR#1 | CR#2 | CR#3 | Avg[1] | STDEV[2] | TTR # 1 | TTR # 2 |
|---|---|---|---|---|---|---|---|
| Harvest | 100 | 100 | 100 | 100 | 0 | 100 | 100 |
| Centrifugation | 113.8 | 97.6 | 96.3 | 102.6 | 9.8 | 188.6 | 71.2 |
| Sartobran ™ filtration | 107.6 | 90.8 | 123.6 | 107.3 | 16.4 | 23.8 | 71.6 |
| Overnight storage | N/D | 76.8 | 85.5 | 81.2 | 6.2 | N/D | N/D |
| Mustang ™ Q | 37.5 | 70.7 | 42.7 | 50.3 | 17.9 | 309.3 | 60.2 |
| UF/DF | 116.7 | 102.8 | 129.9 | 116.5 | 13.6 | 16.5 | 123.4 |
| 0.2 μm filtration | 107.7 | 131.2 | 85.8 | 108.2 | 22.7 | 134.2 | 119.9 |
| Overall yield | 57.7 | 60.8 | 48.8 | 55.8 | 6.2 | 23.9 | 45.4 |

[1,2]Average and STDEV of CR #1-3;
N/D: not determined.

Thus, a purification process for $VSV_{NJ}N4CT_1$-gag1 has been successfully developed and the developed purification conditions were scaled up to 10-L scale (in cell culture volume), still maintaining the same process performance. The process was confirmed by three consistency runs and two tech transfer runs at 6 to 10-L scale (in cell culture volume). A high-quality virus product was produced through this developed process with an acceptable process yield and impurity clearances.

All patents and publications cited throughout this specification are hereby incorporated by reference.

What is claimed is:

1. A process for purifying vesicular stomatitis virus (VSV) from cell culture fluid of a mammalian cell culture infected with VSV, the process comprising:

(a) clarifying the cell culture fluid by low-speed centrifugation or by a 1.0 μm to 4.5 μm depth filtration module and recovering the VSV in the supernatant, wherein the VSV is secreted from the infected mammalian cells;

(b) filtering the supernatant of step (a) through a 0.2 to 0.45 μm filter and recovering the VSV in the filtered solution;

(c) loading the VSV filtered solution of step (b) onto an anion exchange membrane adsorber equilibrated with a first pH buffered salt solution, wherein the salt in the first pH buffered salt solution has an ionic strength of at least about 100 mM to about 400 mM; eluting the VSV from the anion exchange membrane adsorber with a second pH buffered salt solution, wherein the VSV is eluted from the membrane adsorber by adding the second pH buffered salt solution in a single step, wherein the single step elution concentration of the salt is between 500 mM to 750 mM; and recovering the eluted VSV fractions;

(d) purifying the VSV recovered in step (c) by tangential flow filtration (TFF) using a membrane having a molecular weight cutoff between 300 kDa and 1,000 kDa and recovering the VSV in the retentate, and (e) filtering the VSV retentate from step (d) through a 0.2 to 0.22 μm filter and recovering the VSV in the filtered solution, wherein the VSV recovered is at least 90% to about 99% free of cell culture protein and nucleic acid contaminants and further wherein 70-95% of the VSV is recovered.

2. The process of claim 1, wherein the mammalian cells are selected from human embryonic kidney (HEK) cells, HEK 293 cells, Chinese hamster ovary (CHO) cells, baby hamster kidney (BHK) cells, African green monkey kidney (AGMK) cells and AGMK Vero cells.

3. The process of claim 1, wherein the low-speed centrifugation is between 4,400×g to 8,000×g.

4. The process of claim 1, wherein the 0.2 to 0.45 μm filter is a hydrophilic Polyvinylidene Fluoride (PVDF) filter unit, a hydrophilic polyethersulfone filter unit, a cellulose acetate filter unit or a polyethersulfone filter unit.

5. The process of claim 1, wherein the anion exchange membrane adsorber is a quaternary amine membrane adsorber.

6. The process of claim 1, wherein the salt in the first pH buffered salt solution or in the second pH buffered salt solution in step (c) is independently selected from NaCl or KCl.

7. The process of claim 6, wherein the salt in the second pH buffered salt solution is NaCl.

8. The process of claim 7, wherein the second pH buffered salt solution has an elution flow rate of 10 capsule volumes/minute (CV/minute) to 30 CV/minute.

9. The process of claim 1, wherein the first and second buffers independently have a pKa between 6.0 to 8.5.

10. The process of claim 1, wherein the first pH buffered salt solution and second buffered salt solution independently have a pH of 6.5 to about 8.0.

11. The process of claim 1, wherein the first and second buffers are phosphate buffer, N-2-Hydroxyethylpiperazine-N'-2-ethanesulfonic acid (HEPES) buffer or Tris(hydroxymethyl)aminomethane (TRIS).

12. The process of claim 1, wherein the first and second pH buffered salt solutions further comprise sucrose at a concentration of 1.5% to about 5%.

13. The process of claim 1, wherein the TFF membrane has a 300kDa or 750 kDa molecular weight cutoff.

14. The process of claim 1, wherein the TFF membrane is a hollow fiber membrane module.

15. The process of claim 1, wherein the TFF comprises concentrating the VSV recovered from step (c) at least 5×, followed by one to five, buffer exchanges.

16. The process of claim 15, wherein the buffer used in the buffer exchange is a phosphate buffer, HEPES buffer or TRIS buffer.

17. The process of claim 16, wherein the buffer has a concentration of 5 mM to 15 mM phosphate, HEPES or Tris and a pH of about 7.2 to 7.5.

18. The process of claim 16, wherein the buffer further comprises 100 mM to 200 mM NaCl and 3.5% to 4.5% sucrose.

19. The process of claim 1, wherein process steps (a) through (e) are performed at a temperature of 15° C. to 25° C.

20. The process of claim 1, wherein the depth filtration module contains pores of 1 μm to 4.5 μm and the filter material of the module is polypropylene, or cellulosic with inorganic filter aids.

* * * * *